United States Patent
Chung et al.

(10) Patent No.: US 7,223,751 B2
(45) Date of Patent: May 29, 2007

(54) SULFONAMIDE DERIVATIVES, INTERMEDIATE THEREOF, ITS PREPARATION METHODS, AND PHARMACEUTICAL COMPOSITION COMPRISING THE SAME

(75) Inventors: Yong-Jun Chung, Yongin (KR); Kyeong-Ho Lee, Bucheon (KR); Youn-Chul Kim, Suwon (KR); Ho-Jin Park, Seongnam (KR)

(73) Assignee: Kolon Ind. Inc., Kwacheon (KR)

( * ) Notice: Subject to any disclaimer, the term of this patent is extended or adjusted under 35 U.S.C. 154(b) by 452 days.

(21) Appl. No.: 10/475,539

(22) PCT Filed: Apr. 24, 2002

(86) PCT No.: PCT/KR02/00759

§ 371 (c)(1),
(2), (4) Date: Dec. 11, 2003

(87) PCT Pub. No.: WO02/088115

PCT Pub. Date: Nov. 7, 2002

(65) Prior Publication Data

US 2004/0138206 A1    Jul. 15, 2004

(30) Foreign Application Priority Data

| Apr. 26, 2001 | (KR) | ................................ | 2001-22767 |
| Dec. 7, 2001 | (KR) | ................................ | 2001-77522 |
| Mar. 18, 2002 | (KR) | ................................ | 2002-14481 |

(51) Int. Cl.
- *A61K 31/55* (2006.01)
- *A61K 31/497* (2006.01)
- *C07D 243/08* (2006.01)
- *C07D 403/10* (2006.01)
- *C07D 241/04* (2006.01)

(52) U.S. Cl. ............ 514/218; 514/254.01; 514/255.02; 540/575; 544/372; 544/383

(58) Field of Classification Search ............... 514/218, 514/254.01, 255.02; 540/575; 544/372, 544/383
See application file for complete search history.

(56) References Cited

U.S. PATENT DOCUMENTS 5,753,653 A    5/1998   Bender et al.

FOREIGN PATENT DOCUMENTS

| WO | WO 9633172 A | 10/1996 |
| WO | WO 9827069 A | 6/1998 |
| WO | WO-00/44709 A2 | 8/2000 |
| WO | WO 0102371 A | 1/2001 |

OTHER PUBLICATIONS

J. Med. Chem., vol. 43, No. 3, pp. 369-380, 2000.
Levin et al., "The Synthesis and Biological Activity of a Novel Series of Diazepine MMP Inhibitors", Bioorganic & Medicinal Chemistry Letters, pp. 2657-2662 (1998).

*Primary Examiner*—James O. Wilson
*Assistant Examiner*—Ebenezer Sackey
(74) *Attorney, Agent, or Firm*—Birch, Stewart, Kolasch & Birch, LLP

(57) ABSTRACT

The present invention relates to a novel sulfonamide derivatives and novel intermediates thereof, preparation thereof, and a pharmaceutical composition comprising the same, and more particularly, to novel sulfonamide derivatives and intermediates thereof that are used as angiogenesis controlling material and that can inhibit overexpression of matrix metalloproteinase that decomposes protein constituents in extracellular and basement membranes of connective tissues, and preparation methods thereof, and a pharmaceutical composition comprising the same.

11 Claims, No Drawings

SULFONAMIDE DERIVATIVES, INTERMEDIATE THEREOF, ITS PREPARATION METHODS, AND PHARMACEUTICAL COMPOSITION COMPRISING THE SAME

This application is the national phase under 35 U.S.C. § 371 of PCT International Application No. PCT/KRO2/00759 which has an International filing date of Apr. 24, 2002, which designated the United States of America.

BACKGROUND OF THE INVENTION (a) Field of the Invention

The present invention relates to novel sulfonamide derivatives having superior matrix metalloproteinase (MMP) inhibiting activity, and novel intermediates thereof, preparation methods thereof, and a pharmaceutical composition comprising the sulfonamide derivatives.

(b) Description of the Related Art

Angiogenesis, a process during which endothelial cells proliferate from existing capillaries to produce novel capillaries, occurs only under normal physiological functions such as during wound healing, ovulation of females, fetal development processes during pregnancy, etc., and it occurs little under normal conditions exclusive of the above conditions in adults. Angiogenesis is strictly controlled by a balance between angiogenic factors and angiogenesis inhibitors (Folkman, J. and Cotran, Int. Rev. Exp. Pathol. 1976, 16. 207-248. Folkman. J. Nat. Med. 1995. 1, 27-31.).

Erroneous control of angiogenesis is known to cause various diseases (Drug Design and Discovery, 1991, 8, 3. Opthalmol. 1995, 102. 1261-1262. Cell, 1996, 86, 353-364, Biochem. Pharmacol. 2001, 61, 2530270.). Diseases related to angiogenesis occurring in pathological conditions include hemangioma; angiofibroma; arteriosclerosis which is a vascular malformation cardiovascular disease; angiostenosis; edematous sclerosis; etc. Eye diseases caused by angiogenesis include corneal transplantation angiogenesis; angiogenic glaucoma; diabetic retinopathy; angiogenic corneal disease; age-related macular degeneration; pterygium; retinal degeneration; retreolental fibroplasias; granular conjunctivitis; etc. Additionally, skin diseases caused by angiogenesis include chronic inflammatory diseases such as arthritis; psoriasis; telangiectasis; granuloma pyogenicum; sebborhoeic dermatitis; acne; etc., and angiogenisis is also related to periodontal disease. In tumors, cancer cells continuously induce new capillary vessels as pathways to receive nutrient and oxygen for growth thereof and discharge of waste material, and thus angiogenisis is indispensable for growth and metastasis of cancer cells.

The process of angiogenesis generally involves decomposition of the basement membrane of blood vessels by protease, formation of vascular lumen by differentiation, proliferation, and migration of endothelial cells, and reconstruction of blood vessels. Protease involved in this process is referred to as matrix metalloproteinase (hereinafter referred to as 'MMP' enzyme).

Matrix metalloproteinase (MMP) is an enzyme secreted from cells such as polymorphonuclear neutrophile, macrophage, fibroblast, and bone cells, etc. MMP is known to decompose protein constituents of the extracellular matrix to be involved in wound healing, angiogenesis, pregnancy, decomposition and reconstruction of connective tissue, etc. Overexpression of MMP is known to be a main cause of various diseases including invasion and metastasis of tumors, and arthritis, by unwanted decomposition of connective tissue. The enzyme is involved in various diseases such as arthritis, tumor growth and metastasis, periodontal disease, multiple sclerosis, etc.

MMP enzymes are a family of metalloproteinase, having zinc at their active site, and they decompose and reconstruct proteins such as membrane collagen, aggrecan, fibronectin, and laminin that form structural proteins in an extracellular matrix. Functions of the enzyme in organisms are naturally inhibited by intrinsic tissue inhibitors of metalloprotease (TIMPs), but an imbalance thereof causes overexpression and activation of MMPs to cause decomposition of tissue. Functions of MMPs play important roles in the development of chronic diseases such as multiple sclerosis, arthritis, fibrosis and other inflammation, and growth and metastasis of malignant tumors. For this reason, MMPs are attractive targets as inhibitors of development and treatment of such diseases.

Up to now, 17 kinds of MMP enzymes in humans have been known, and they show many similarities therebetween. They are largely divided into collagenase, stromelysin, gelatinase, matrilysin, metalloelastase, and membrane-type (MT) MMP enzymes.

Epileptic enzyme fibroblast collagenase pertains to MMP-1, and substrates of the enzyme thereof are collagen type I, II, III, VII, VIII, X, and gelatin. 72-Kda gelatinase A pertains to MMP-2, and substrates of the enzyme thereof are gelatin, collagen type IV, V, VII, X, elastin, and fibronectin. Stormelysin-1 pertains to MMP-3, and substrates of the enzyme thereof are proteoglycan, fibronectin, laminin, procolagenase, collagen type IV, V, IX, X, and elastin. Matrilysin pertains to MMP-7, and substrates of the enzyme thereof are proteoglycan, fibronectin, laminin, procolagenase, gelatin, collagen type IV, elastin, and urokinase. Polymorphonuclear leukocyte collagenase pertains to MMP-8, and substrates of the enzyme thereof are the same as those of MMP-1. Stormelysin-2 pertains to MMP-10, and substrates of the enzyme thereof are the same as those of MMP-3. Stormelysin-3 pertains to MMP-11, and substrates of the enzyme thereof are laminin and fibronectin. Macrophage metalloelastase pertains to MMP-12, and substrates of the enzyme thereof are elastin and fibronectin. Up to now, targeted MMPs include MMP-1, MMP-2, MMP-3, MMP-7, MMP-8, MMP-9, MMP-13, membrane-type-1-MMP (MT1-MMP), etc.

During carcinogenesis, various MMPs are simultaneously produced to be involved in growth and metastasis of tumors. In metastasis of cancer cells, malignant cancer cells are separated from a primary tumor and produced MMPs to decompose main ingredients of extracellular matrices, collagen, fibronectin, proteoglycan, etc., and cause migration and proliferation of endothelial cells. In this process, MMPs such as MMP-1, MMP-2, MMP9, etc. act. Therefore, inhibitors of these MMP enzymes can be used for a novel anticancer drug blocking growth and metastasis of cancer cells. Collagen, which is a constitutional ingredient of the main protein of an extracellular matrix, maintains its structural form in various tissues and provides physical strength, and is involved in various processes such as cell attachment, migration, differentiation, etc. Turnover of collagen is required for reconstruction of connective tissue during growth and development of cells, and it is involved in arthritis, glomerulonephritis, atherosclerosis, tissue ulceration, periodontal disease, fibrotic lung disease, and pathological processes accompanying invasion and metastasis of cancer cells. Particularly, it has been clarified that during carcinogenesis, in cancer invasion and metastasis stages, MMP-2 and MMP-9 are excessively secreted. MMP-2, which is the enzyme mostly expressed in bodies, decomposes collagen type V, VII, X, fibronectin, elastin, and all forms of unfolded collagen, as well as collagen type IV. Type IV collagenase MMP-2 and MMP-9 decompose type IV collagen, which is a main ingredient of basement membranes, which are the first barrier to cancer metastasis, and they are the most important enzymes involved in invasion and metastasis of cancer cells. Therefore, a type IV collagenase MMP-2 and MMP-9 inhibitor can be used for treatment of cancer invasion and metastasis, and for rheumatoid and periodontal disease, as well as for corneal ulcers caused by decomposition of collagenic connective tissue.

Collagenase that is secreted by fibroblast, polymorphonuclear leukocyte, epithelia, and macrophage cells is an important enzyme in periodontal disease. First, an endotoxin such as lipopolysaccharide is secreted to periodontal tissue due to anaerobic gram negative infection, and thereby tissues are directly destroyed, or cytokines such as interleukin and prostaglandin are secreted because of immunization of bodies, to cause inflammation. Collagen, a matrix of periodontal tissues, is decomposed by collagenase secreted by stimulation of these inflammation media and bacterial collagenase to cause gingival inflammation, which, if left, progresses toward periodontal disease. In addition, MMP-3 and MMP-8 also reduce proteoglycan, which is a main polymer ingredient of connective tissues. Thus, an inhibitor for these enzymes (MMP-3, MMP-8) can also be used for treating periodontal disease.

Arthritis, a representative inflammatory disease, occurs because of autoimmunization, but as the disease progresses, chronic inflammation occurring in the synovial cavity between articulations causes angiogenesis to destroy connective tissues without blood vessels. With the aid of inflammation-causing cytokine, synovial cells and endothelial cells that proliferate in the synovial cavity progress angiogenesis, thereby forming a connective tissue layer, an articular disc, to destroy connective tissues functioning as a cushion (Koch, A. E. Polverini, P, J., Leibovich, S. J., Arthritis Rheum. 1986, 29, 471. Koch, A. E., Arthritis Rheum. 1998, 41, 951); It has been clarified that MMP enzymes decompose the main ingredients of connective tissue, collagen and proteoglycan (Sapolsky, A. I., Keiser, H., Howell, D. S., Woessner, J. F., Jr. J. Clin. Invest. 1976, 58, 1030). They have been cloned from breast cancer cells, and clarified to be involved in arthritis (Freiji, J. M., Diez-Itza, I., Balbin, M., Sanchez, L. M., Blasco, R., Tolivia, J., Lopez-Otin, C., J. Biol. Chem. 1994, 269, 16766). In addition, the main substrate of MMP-13 is type II collagen which is a main constructional ingredient of articular cartilage, and as it has been clarified that a concentration of the enzyme increases in human bone and joint tissues and the enzyme is produced by chondrocyte, it has also been clarified to be involvedd in arthritis, and thus an inhibitor for the enzyme can be used for an arthritis-treating agent.

A TNF-α converting enzyme (TACE) catalyzes formation of TNF-α from a membrane-bound TNF-α protein precursor. TNF-α is a pro-inflamatory-cytokine involved in anti-tumor processes as well as in rheumatoid arthritis, septic shock, transplantation rejection, insulin tolerance, and HIV inflammation; and it is also known to mediate congestive heart failure, cachexia, anorexia, inflammation, fever, inflammatory disease of the central nervous system and inflammatory bowel disease. It has been proven in a study using transfected animals and an antibody for TNF-α that blocking TNF-α formation inhibits progress of arthritis (Rankin, E. C., Choy, E. H., Kassimos, D., Kingsley, G. H., Sopwith, A. M., Isenberg, D. A., Panayi, G. S. Br. J. Rheurmatol. 1995, 34, 334). Therefore, a low molecular inhibitor for MMP and TACE is expected to have potential for treating various disease symptoms including arthritis.

Eye diseases causing blindness a few hundred times every year are also caused by angiogenesis (Jeffrey, M. I., Takayuki, A., J. Clin. Invest. 1999, 103, 1231). Diseases such as macular degeneration occurring in old persons, diabetic retinopathy, retinopathy of prematurity, angiogenic glaucoma, and corneal disease of angiogenesis are caused by angiogenesis (Adamin, A. P., Aiello, L. P., D'Amato, R. A., Angiogenesis 1999, 3, 9). Diabetic retinopathy is a complication of diabetes, wherein capillaries in retina infiltrate into the vitreous body by angiogenesis to cause blindness. Eyes are tissue without blood vessels, and growth of blood vessels causes blindness. Eye disease caused by angiogenesis has no appropriate treating agent, and presently, steroids or antibiotics are used. If the disease is more progressed, blood vessels are cauterized or photocoagulated, but the effects are temporary and cannot block proliferation of blood vessels, and thus the disease relapses. Therefore, the most basic treatment method is to block angiogenesis.

Additionally, psoriasis characterized by red spots and scale on the skin is a chronic proliferatory skin disease, and this is also not easily healed and it involves pain and malformation. For an ordinary person, horny cells(or corneocyte) proliferate once a month, while for a patent with psoriasis, they proliferate at least once a week. For such fast proliferation, a great deal of blood must be supplied, and thus angiogenesis actively occurs (Folkman, J. J. Invest. Dermatol. 1972, 59, 40). Thus, an angiogenesis inhibitor can be used as a novel treating agent of dermatological diseases such psoriasis.

It is known that since the proteinases are involved in various physiological processes such as embryogenesis, tissue formation, salivary gland formation, odontogenesis, etc., they are involved in various diseases of pathological processes such as cancer metastasis, periodontal disease, rheumatoid arthritis, inflammation, hyperparathyroidism, diabetes, corneal ulcers, osteoporosis, stomach ulcers, wounds, wrinkles, acne, AIDS, burns, arteriosclerosis, bone fractures, etc.

MMP inhibitors that can be used for treating agents of various diseases have been subject to many patents and patent applications, as follows. Specifically, they are described in U.S. Pat. No. 5,189,178; U.S. Pat. No. 5,455, 258; U.S. Pat. No. 5,506,242; U.S. Pat. No. 5,672,615; U.S. Pat. No. 5,756,545; U.S. Pat. No. 5,804,593; U.S. Pat. No. 5,817,822; U.S. Pat. No. 5,859,061; U.S. Pat. No. 5,861,510; U.S. Pat. No. 5,962,471; U.S. Pat. No. 5,985,900; U.S. Pat. No. 6,022,873; U.S. Pat. No. 6,022,893; U.S. Pat. No. 6,071,903; U.S. Pat. No. 6,121,272; U.S. Pat. No. 6,143,744; U.S. Pat. No. 6,150,394; U.S. Pat. No. 6,153,612; U.S. Pat. No. 6,156,798; U.S. Pat. No. 6,159,995; and U.S. Pat. No. 6,612, 821.

As explained, through recent studies of MMP inhibitors, efforts to prevent and treat various diseases and pathological processes such as cancer metastasis, periodontal disease, rheumatoid arthritis, inflammation, hyperparathyroidism, diabetes, corneal ulcers, osteoporosis, stomach ulcers, wounds, wrinkles, acne, AIDS, burns, arteriosclerosis, bone fractures, etc. have been extensively made, but satisfactory effects for inhibiting MMP have not been obtained.

SUMMARY OF THE INVENTION

In order to solve the problems of the prior art, it is an object of the present invention to provide novel sulfonamide derivatives having superior enzyme inhibitory activities to the existing matrix metalloproteinase inhibitor by acting as angiogenesis inhibitors.

It is another object of the present invention to provide novel intermediates of the sulfonamide derivatives.

It is another object of the present invention to provide a process for preparing novel sulfonamide derivatives and intermediates thereof.

It is another object of the present invention to provide a pharmaceutical composition for treating various diseases, acting as a matrix metalloproteinase inhibitor by comprising the sulfonamide derivatives, pharmaceutically acceptable salts, or solvates thereof.

In order to achieve these objects, the present invention provides a compound represented by the following Chemical Formula 1, or optical isomers, pharmaceutically acceptable salts, or solvates thereof:

[Chemical Formula 1]

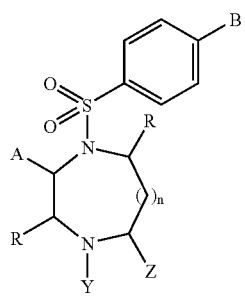

wherein, n is 0, 1, 2 or 3;

A is $CO_2H$, CONHOH, $CH_2SH$, or $CH_2OH$;

B is hydrogen; a C1-18 alkyl group; a nitro group; an aryl group; a heteroaryl group; a pyrrole group; a halogen atom; a C1-8 O-lower alkyl group; an O-aryl group; an N-lower alkyl group; an S-lower alkyl group;

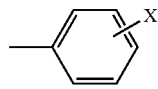

(X is hydrogen, a C1-8 lower alkyl group, a C9-20 higher alkyl group, a C9-20 higher alkyl group comprising a double bond, an aryl group, a heteroaryl group, a halogen atom, an O-lower alkyl group, an O-aryl group, an O-heteroaryl group, an N-aryl group, an N-heteroaryl group, an S-aryl group, an S-heteroaryl group, a C1-20 alkyl-amine derivative, a C1-20 alkyl-carboxylic acid derivative, an amine group or nitro group); an amide compound of CONHR or NHCOR; a carbamate compound of NHCOOR; or a urea compound of NHCONHR (R is hydrogen, a C1-9 lower alkyl group, an aryl group, a heteroaryl, a tetragonal to octagonal heterocyclic compound, or a C1-8 lower alkyl group substituted by a tetragonal to octagonal heterocyclic compound);

R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound;

Z is hydrogen, oxygen, or sulfur, and in the case Z is oxygen or sulfur, it takes a double bond; and Y is hydrogen; a C1-8 lower alkyl group; an aryl group; a heteroaryl; a C1-8 lower alkyl group substituted by a tetragonal to octagonal cyclic compound; a C1-8 lower alkyl group substituted by a tetragonal to octagonal heterocyclic compound; an amide compound of CONHR or NHCOR; a carbamate of NHCOOR; a urea compound of NHCONHR; a C1-8 lower alkyl group having a double bond or a triple bond; or a C9-20 higher alkyl group having a double bond or a triple bond (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by tetragonal to octagonal cyclic compound).

The present invention also provides a process for preparing a compound of the Chemical Formula 1 wherein A is CONHOH, by reacting a compound of the following Chemical Formula 2 with $NH_2OH$ and KOH, or $NH_2OH$ in the presence of $AlCl_3$.

[Chemical Formula 2]

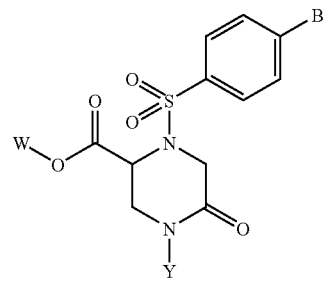

wherein,

B is hydrogen; a C1-8 lower alkyl group; a nitro group; an aryl group; a heteroaryl group; a pyrrole group; a halogen atom; a C1-9 O-lower alkyl group; an O-aryl group; an N-lower alkyl group; an S-lower alkyl group;

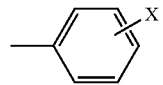

(X is hydrogen, a C1-8 lower alkyl group, a C9-20 higher alkyl group, a C9-20 higher alkyl group comprising a double bond, an aryl group, a heteroaryl group, a halogen atom, an O-lower alkyl group, an O-aryl group, an O-heteroaryl group, an N-aryl group, an N-heteroaryl group, an S-aryl group, an S-heteroaryl group, a C1-20 alkyl amine derivative, a C1-20 alkyl carboxylic acid derivative, an amine group, or a nitro group); an amide compound of CONHR or NHCOR; a carbamate compound of NHCOOR; or a urea compound of NHCONHR (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound);

W is hydrogen, or a methyl, ethyl, t-butyl, or C1-8 lower alkyl group comprising a benzyl group; and Y is hydrogen; a C1-18 alkyl group; an aryl group; a heteroaryl; a C1-8 lower alkyl group substituted by a tetragonal to octagonal cyclic compound; a C1-8 lower alkyl group substituted by a tetragonal to octagonal heterocyclic compound; an amide compound of CONHR or NHCOR; a carbamate compound of NHCOOR; a urea compound of NHCONHR; a C1-8 lower alkyl group having a double bond or a triple bond; or a C9-20 higher alkyl group having a double bond or a triple bond (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound).

The present invention also provides a process for preparing a compound of the Chemical Formula 1 wherein A is $CO_2H$, by hydrogenating a compound of the Chemical Formula 2 in the presence of an inorganic base, acid-base, or a Pd/C catalyst.

The present invention also provides a process for preparing a compound of the Chemical Formula 1 wherein A is $CH_2OH$, by dissolving a compound of the Chemical Formula 2 in methanol, ethanol, or THF, and introducing a reducing agent therein.

The present invention also provides a process for preparing a compound of the Chemical Formula wherein A is $CH_2SH$, by Mitsunobu-reacting a compound of the Chemical Formula 1, wherein A is $CH_2OH$, and adding NaOH thereto.

The present invention also provides a compound represented by the following Chemical Formula 2, optical isomers, pharmaceutically acceptable salts, or solvates thereof:

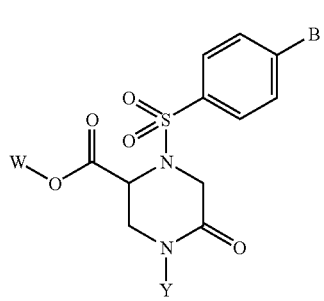

[Chemical Formula 2]

(wherein B, W, and Y are as defined above.)

The present invention also provides a process for preparing a compound represented by the above Chemical Formula 2, by reacting a compound of the following Chemical Formula 3 with methanesulfonyl chloride, toluenesulfonyl chloride, or triflic anhydride in the presence of a base, and reacting it with a primary amine.

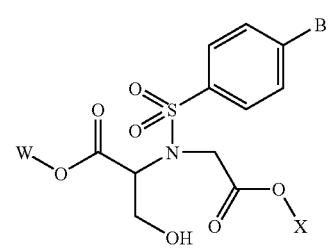

[Chemical Formula 3]

wherein,

B is hydrogen; a C1-8 lower alkyl group; a nitro group; an aryl group; a heteroaryl group; a pyrrole group; a halogen atom; a C1-9 O-lower alkyl group; an O-aryl group; an N-lower alkyl group; an S-lower alkyl group;

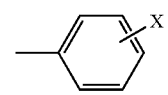

(X is hydrogen, a C1-8 lower alkyl group, a C9-20 higher alkyl group, a C9-20 higher alkyl group comprising a double bond, an aryl group, a heteroaryl group, a halogen atom, an O-lower alkyl group, an O-aryl group, an O-heteroaryl group, an N-aryl group, an N-heteroaryl group, an S-aryl group, an S-heteroaryl group, a C1-20 alkyl amine derivative, a C1-20 alkyl carboxylic acid derivative, an amine group, or a nitro group); an amide compound of CONHR or NHCOR; a carbamate compound of NHCOOR; or a urea compound of NHCONHR (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound);

W and X are independently or simultaneously hydrogen, or a methyl, ethyl, t-butyl, or C1-8 lower alkyl group comprising a benzyl group. The present invention also provides a compound represented by the following Chemical Formula 3, optical isomers, pharmaceutically acceptable salts, or solvates thereof:

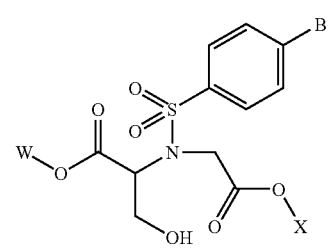

[Chemical Formula 3]

(wherein B, W, and X are as defined above.)

The present invention also provides a process for preparing a compound represented by the above Chemical Formula 3, by reacting a compound of the following Chemical Formula 4 with a halogen compound, an ethyl bromoacetate in the presence of inorganic base, and DMF or acetonitrile solvent.

[Chemical Formula 4]

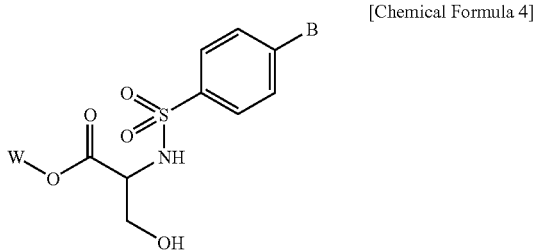

(wherein,

B is hydrogen; a C1-8 lower alkyl group; a nitro group; an aryl group; a heteroaryl group; a pyrrole group; a halogen atom; a C1-8 O-lower alkyl group; an O-aryl group; an N-lower alkyl group; an S-lower alkyl group;

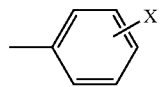

(X is hydrogen, a C1-8 lower alkyl group, a C9-20 higher alkyl group, a C9-20 higher alkyl group comprising a double bond, an aryl group, a heteroaryl group, a halogen atom, an O-lower alkyl group, an O-aryl group, an O-heteroaryl group, an N-aryl group, an N-heteroaryl group, an S-aryl group, an S-heteroaryl group, a C1-20 alkyl-amine derivative, a C1-20 alkyl-carboxylic acid derivative, an amine group, or a nitro group.); an amide compound of CONHR or NHCOR; a carbamate compound of NHCOOR; or a urea compound of NHCONHR (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound.); and W is a methyl, ethyl, t-butyl, or C-18 lower alkyl group comprising a benzyl group.)

The present invention also provides a pharmaceutical composition comprising the compound of the Chemical Formula 1, optical isomers, pharmaceutically acceptable salts, or solvates thereof as an active ingredient.

The present invention also provides a method for treating cancer metastasis and solid cancer using the compound of the Chemical Formula 1.

The present invention also provides a method for treating diseases related to angiogenesis using the compound of the Chemical Formula 1.

DETAILED DESCRIPTION AND THE PREFERRED EMBODIMENTS

The present invention will now be explained in detail.

The present invention relates to sulfonamide derivatives of the above Chemical Formula 1 that can be used as angiogenesis controlling material to inhibit overexpression of matrix metalloproteinase, which decomposes the extracellular matrix of connective tissue and protein constituents of basement membranes, and thus has superior enzyme inhibitory activity to the existing matrix metalloproteinase, and a process for preparing the same.

The compound of the above Chemical Formula 1 according to the present invention is a compound substituted with a phenyl sulfonyl group at position 4, and it is used as an angiogenesis controlling material to show superior angiogenesis inhibiting activity.

The compound of the present invention is preferably a compound of the Chemical Formula 1, wherein A is CONHOH.

Additionally, the compound of the present invention is preferably a compound of the Chemical Formula 1, wherein A is $CO_2H$.

Additionally, the compound of the present invention is preferably a compound of the Chemical Formula 1, wherein A is $CH_2SH$.

Additionally, the compound of the present invention is preferably a compound of the Chemical Formula 1, wherein A is $CH_2OH$.

A process for preparing the compound of the Chemical Formula 1, wherein A is CONHOH is as shown in the following scheme 1.

[Scheme 1]

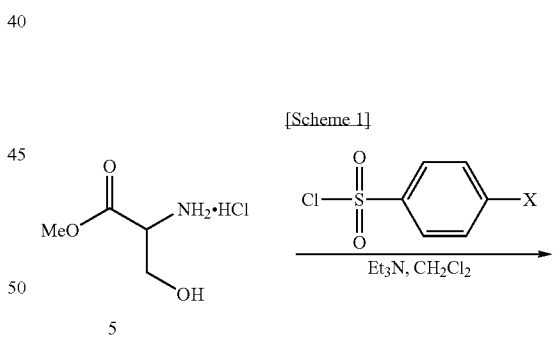

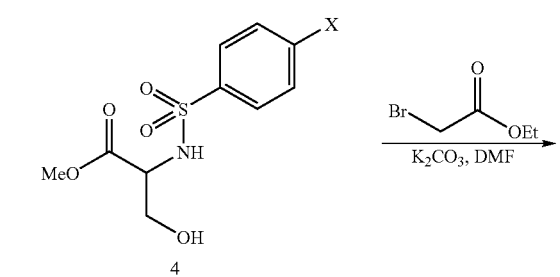

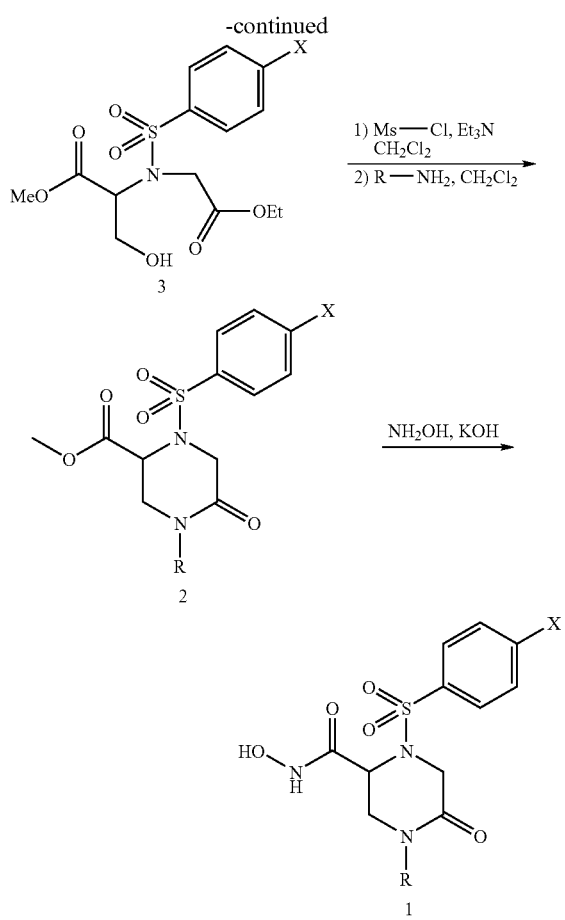

As shown in scheme 1, an amino acid derivative of the Chemical Formula 5 such as D-serine methyl ester HCl or D-threonine methyl ester HCl is treated with benzenesulfonyl chloride in a solution comprising 2 equivalents of $Et_3N$ and a catalytic amount of 4-dimethylaminopyridine, to prepare a compound of the Chemical Formula 4.

Then, the compound of the Chemical Formula 4 is dissolved in a solvent such as DMF or acetonitrile, an inorganic base such as potassium carbonate is introduced therein, and it is reacted with ethylbromoacetate to prepare a compound of the Chemical Formula 3. More preferably, the compound of the Chemical Formula 4 is reacted with ethylbromoacetate in a solvent such as DMF or acetonitrile in which an inorganic salt such as potassium carbonate and a catalytic amount of $Et_3N$ is introduced to prepare a compound of the Chemical Formula 3. According to the above process, the process time can be reduced, and the yield can be greatly increased. In a solvent such as DMF or acetonitrile, using 1.5 to 3 equivalents of potassium carbonate and a catalytic amount of $Et_3N$, the reaction is conducted at 25 to 90° C. for 3 to 8 hours to greatly improve the yield to 65 to 85% compared to the case of using only potassium carbonate.

Additionally, in a solvent such as DMF or acetonitrile, a compound having an appropriate alcohol protection group such as trimethylsilyl, an inorganic salt such as potassium carbonate, and a catalytic amount of $Et_3N$ are introduced, and an alcohol group of the compound of the Chemical Formula 4 is reacted with ethylbromoacetate to prepare a compound of the Chemical Formula 3b having an alcohol protection group. The compound having an alcohol protection group includes, in addition to the above-mentioned trimethylsilyl, a lower alkyl; a substituted methyl, ethyl, or benzyl ether such as methoxy methyl, 1-ethoxyethyl, or p-methoxybenzyl; an ester such as formate, acetate, etc.; and a carbonate such as methylcarbonate, etc.

Then, the compound of the Chemical Formula 3 is reacted with a compound that increases the reactivity of the alcohol group such as methanesulfonyl chloride, toluenesulfonyl chloride, or triflic anhydride in a dichloromethane solvent in which a base such as $Et_3N$ is introduced, and it is reacted with various agents having a primary amine group such as ammonia or methylamine in an appropriate solvent such as dioxane in which a base such as $Et_3N$ is introduced, to prepare a compound 2.

In addition, in the case of a compound of the Chemical Formula 3 having an alcohol protection group, the alcohol protection group is removed, and then the compound is reacted with a compound that increases reactivity of the alcohol group such as methanesulfonyl chloride, toluenesulfonyl chloride, or triflic anhydride in the presence of a base such as $Et_3N$ in a dichloromethane solvent, and it is then reacted with various agents having a free amine group such as ammonia in an appropriate solvent such as dioxane in the presence of base such as $Et_3N$, to prepare a compound 2.

Then, the compound 2 is dissolved in 1.7 M of a methanol solution of hydroxylamine ($NH_2OH$) (prepared from hydroxylamine and potassium hydroxide (KOH) according to Fieser and Fieser, Vol. 1, p. 478 process) to prepare a compound of the Chemical Formula 1. Instead of the methanol solution of hydroxylamine, hydroxylamine ($NH_2OH$) and a metal compound such as aluminum chloride ($AlCl_3$) can be used.

In addition, a process for preparing a compound of the Chemical Formula 1 wherein A is $CO_2H$ is as shown in the following Scheme 2.

[Scheme 2]

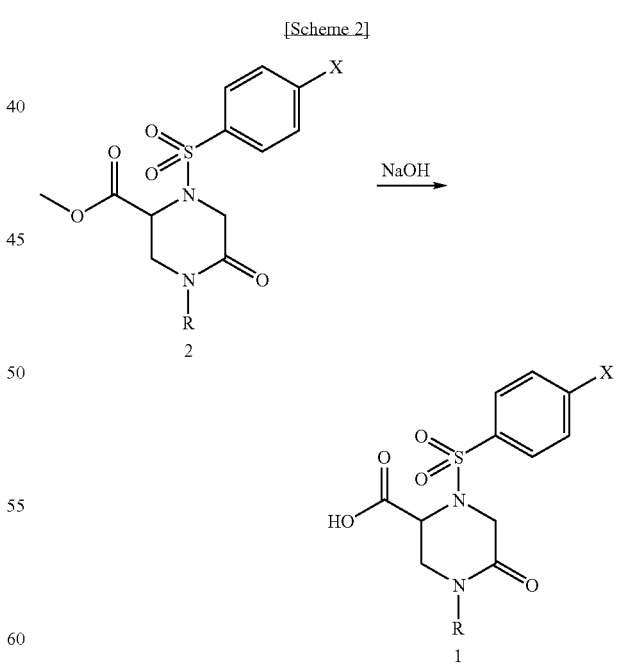

As shown in the scheme 2, the compound 2 is dissolved in a solvent such as methanol, ethanol, or THF and it is reacted with NaOH, potassium hydroxide (KOH), LiOH, or $Ba(OH)_2$ to prepare a compound of the Chemical Formula 1, wherein A is $CO_2H$.

In addition, a process for preparing a compound of the Chemical Formula 1 wherein A is CH$_2$SH is as shown in the following Scheme 3.

[Scheme 3]

As shown in the sheme 3, the compound 2 is dissolved in methanol, ethanol, or a THF solvent, and an ester group of the compound 2. is converted into an alcohol group using a reducing agent such as NaBH$_4$ to prepare a compound of the Chemical Formula 1a. Then, the compound 1a is converted into a thioester using thioacetic acid by a Mitsunobu reaction, and NaOH is added thereto to prepare a compound of the Chemical Formula 1b, i.e., a compound of the Chemical Formula 1 wherein A is CH$_2$SH.

In addition, in the case B when the compound of the Chemical Formula 1 forms a pyrrole ring, a process for preparing the compound of the Chemical Formula 1 is as shown in Scheme 4.

[Scheme 4]

As shown in the Scheme 4, a compound 6 having a 4-nitrobenzenesulfonyl group is hydrogenated using SnCl$_2$ or in the presence of a metal catalyst such as Pd/C, to prepare a compound 2c. Then, the compound 2c is condensed with 2,5-dimethoxytetrahydrofuran to prepare a compound 2d. The present invention is a compound of the Chemical Formula 1 wherein B forms a pyrrole ring prepared by the same reaction as used in the Equations 1, 2, and 3 using the compound 2c.

In addition, in the case of a compound of the Chemical Formula 1 wherein B has an amide group, a process for preparing the same is as shown in Scheme 5.

[Scheme 5]

-continued

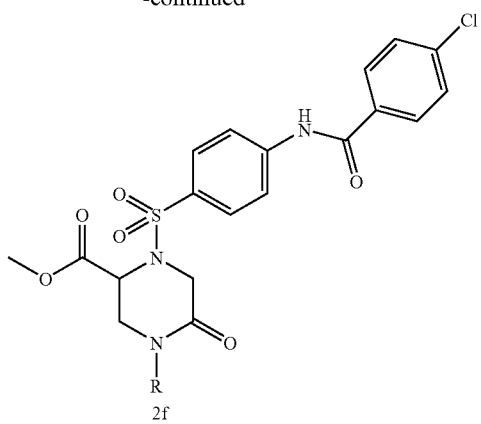

2f

As shown in the Scheme 5, the compound 2c is reacted with 4-chlorobenzoyl chloride in the presence of Et₃N to prepare a compound 2f. Then, from the compound 2f, a compound of the Chemical Formula 1 wherein B has an amide group is prepared using the same reaction as used in the Schemes 1, 2, and 3.

The present invention also provides a pharmaceutical composition comprising the compound of the Chemical Formula 1, optical isomers, and pharmaceutically acceptable salts or solvates thereof as an active ingredient.

In the pharmaceutical composition of the present invention, the contents of the compound of the Chemical Formula 1 can be controlled according to the purpose of its use, and they are not specifically limited. The pharmaceutical composition of the present invention can be administrated to a patient by oral or non-oral administration in any form, including solid or liquid. The pharmaceutical composition of the present invention may further comprise a pharmaceutically acceptable liquid or solid carrier.

The solid preparation includes a powder, a tablet, dispersable granules or a capsule, and a solid dosage form suitable for oral administration includes a tablet, a powder, or a capsule. An appropriate excipient includes a diluent, a flavoring agent, a solubilizer, a lubricant, a suspension, a binder, and/or a bulking agent. In the case of a powder or capsule, a vehicle can comprise 5 to 70%, and preferably 10 to 70% of the powdered active ingredient. A suitable solid vehicle or excipient includes corn starch, magnesium stearate, film, polyethyleneglycol, talc, sugar, lactose, pectin, dextrin, starch, gelatin, hydroxypropylmethylcellulose, methylcellulose, sodium carboxymethylcellulose, titan dixode, a low melting point wax, cocoa butter, etc.

The liquid preparation may be a solution, a suspension, or an emulsion. As examples, in the case of a non-oral injection solution, water or a mixed solution of water and propyleneglycol can be used, and the solution is prepared so that its isotonicity, pH etc. are suitable for a living body system. A liquid phase preparation may also be formed of a polyethylene glycol aqueous solution. An aqueous solution suitable for oral administration can be prepared by dissolving an active ingredient in water and adding an appropriate flavoring agent, coloring agent, stabilizer, and thickener. An aqueous suspension suitable for oral administration can be prepared by dispersing the powdered active ingredient in a viscous material such as natural or synthetic gum, resin, methylcellulose, sodium carboxymethylcellulose, or other known suspensions.

A preferable pharmaceutical preparation is a Unit dosage form. The preparation is finely divided into a unit administration form comprising an appropriate amount of active ingredient. The unit dosage form can be a packaged preparation comprising a separated amount of the preparation, for example a packaged tablet or capsule, or a powder in a vial or ampule.

As explained, the pharmaceutical composition of the present invention comprising the compound of the Chemical Formula 1 as an active ingredient acts as a superior matrix metalloproteinase inhibitor and can be used for a treating agent of various diseases and pathological processes such as cancer metastasis, periodontal disease, rheumatoid arthritis, inflammation, hyperparathyroidism, diabetes, corneal ulcers, osteoporosis, stomach ulcers, wounds, wrinkles, acne, AIDS, burns, arteriosclerosis, bone fractures, etc. The pharmaceutical composition comprising the compound of the Chemical Formula 1 is preferably an anticancer drug.

The present invention will be explained in more detail with reference to the following Examples. However, these are to illustrate the present invention, and the present invention is not limited to them.

EXAMPLE 1

Synthesis of Methyl 3-hydroxy-2-(4-methoxy-benzenesulfonylamino)propionate

DL-serine methylester HCl (14,6 g, 93,8 mmol) of the Chemical Formula 5 was suspended in 400 mL of dichloromethane, and Et₃N (29 Ml, 206 mmol). and a catalytic amount of 4-dimethylaminopyridine were introduced therein while maintaining the temperature at 0° C., and 4-methoxybenzene-sulfonyl chloride (19.2 g 94 mmol) was add dropwise. They were stirred at room temperature for 20 hours, washed with 200 mL of distilled water, dried, and concentrated under reduced pressure to obtain a yellow solid title compound (26.5 g, yield 97%).

EXAMPLE 2

Synthesis of Methyl 2-[ethoxycarbonylmethyl-(4-methoxy-benzenesulfonyl)-amino]-3-hydroxy-propionate The compound of Example 1 (7.2 g, 24.8 mmol) and anhydrous potassium carbonate (7 g, 50 mmol) were suspended in DMF (50 mL), and ethyl bromoacetate (4.5 Ml, 37 mmol) was added dropwise. After stirring for 40 hours, 50 ml of distilled water and 100 mL of ethyl acetated were introduced and stirred to separate layers. The supernatant was washed with a 1N HCl aqueous solution (50 mL), a saturated NaHCO₃ aqueous solution (50 mL), and distilled water (100 mL), and it was dried and concentrated under reduced pressure. The mixture was separated using hexane and ethylacetate (2:1) in a silica gel column to obtain a yellow thick oily title compound (5.04 g, yield 54%).

$^1$H NMR (CDCl₃, 400 MHz) δ 1.28(m, 3H), 3.58(s, 3H), 3.63(m, 1H), 3.85(s, 3H), 3.96(d, J=18.8 Hz, 1H), 4.09(m, 1H), 4.23(m, 2H), 4.41 (d, J=18.8 Hz, 1H), 4.73(dd, J=9.5, 4.2 Hz,1H), 6.96(d, J=8.8 Hz, 2H), 7.77(d, J=8.8 Hz, 2H).

EXAMPLE 3

Synthesis of Methyl 2-[ethoxycarbonylmethyl-(4-methoxy-benzenesulfonyl)-amino]3-hydroxy-propionate The compound of Example 1 (5.65 g, 19.5 mmol) and anhydrous potassium carbonate anhydrous (8 g, 60 mmol) were suspended in DMF (35 mL), a catalytic amount of Et$_3$N was introduced, and ethyl bromoacetate (4.3 mL, 40 mmol) was added dropwise. After stirring for 5 hours, 50 mL of distilled water and 100 mL of ethyl acetate were introduced and stirred to separate layers. The supernatant was washed with a 1N HCl aqueous solution (50 mL), a saturated NaHCO$_3$ aqueous solution (50 mL), and distilled water (100 mL), and it was dried and concentrated under reduced pressure. The mixture was separated using hexane and ethylacetate (2:1) in a silica gel column to obtain a yellow thick oily title compound (5.26 g, yield 72%).

$^1$H NMR (CDCl$_3$, 400 MHz) δ 1.28(m, 3H), 3.58(s, 3H), 3.63(m, 1H), 3.85(s, 3H), 3.96(d, J=18.8 Hz, 1H), 4.09(m, 1H), 4.23(m, 2H), 4.41(d, J=18.8 Hz, 1H), 4.73(dd, J=9.5, 4.2 Hz, 1H), 6.96(d, J=8.8 Hz, 2H), 7.77(d, J=8.8 Hz, 2H).

EXAMPLE 4

Synthesis of Methyl 1-(4-methoxy-benzenesulfonyl)-5-oxo-piperazine-2-carboxylate The compound of Example 3 (1.97 f, 6.0 mmol) was suspended in 50 mL of dichloromethane, and Et$_3$N (1.2 Ml, 8.4 mmol) and methane sulfonyl chloride (0.56 mL, 7.2 mmol) were added while maintaining the temperature at 0° C. After stirring at room temperature for 16 hours, the reactant was washed with 50 mL of distilled water, and it was dried and distilled under reduced pressure. It was dissolved in 15 mL of 1,4-dioxane, and Et$_3$N (1.6 mL, 12 mmol) and 28% ammonia water (0.73 mL, 1 mmol) were added. After stirring for 24 hours, 50 mL of distilled water and 100 mL of ethyl acetate were introduced, and the layers were separated. The supernatant was collected and dried, concentrated under reduced pressure, and separated in a silica gel column to obtain a yellow oily title compound 4a (0.75 g, yield 38%).

$^1$H NMR (CDCl$_3$, 400 MHz) δ 3.57(s, 3H), 3.72(t, J=3.1 Hz, 1H), 3.87(s, 3H), 3.92(d, J=17.3 Hz, 1H), 4.21(d, J=17.1 Hz, 1H), 4.86(t, J=3.3 Hz, 1H), 6.31(br,1H), 6.99(dd, J=7.1, 1.9 Hz, 2H), 7.73(dd, J=6.8, 2.0 Hz, 2H).

EXAMPLE 5

Synthesis of 1-(4-Methoxy-benzenesulfonyl)-5-oxo-piperazine-2-hydroxamate)

To the compound of Example 4 (0.49 g, 1.49 mmol), 10 mL of a 1.7 M hydroxylamine (H$_2$NOH) solution (prepared from hydroxylamine and potassium hydroxide (KOH) according to Fieser and Fieser, Vol. 1, p 478 method) was added and stirred for 5 hours. After 5 hours, the reactant was acidified with a 2 N HCl aqueous solution and the pH was made neutral with a saturated NaHCO$_3$ aqueous solution, and then it was extracted with ethyl acetate, and dried and concentrated under reduced pressure. The reactant was dissolved with ethyl acetate and methanol (MeOH), and then hexane was added thereto to obtain a white solid title compound (0.22 g, yield 45%) by recrystallization.

$^1$H NMR (DMSO-d$_6$, 400 MHz) δ 3.20(m, 2H), 3.72(t, J=3.1 Hz, 1H), 3.83(s, 3H), 3.88(br d, 1H), 4.09(s, 1H), 4.32(s, 1H), 7.09(d, J=8.8 Hz, 2H), 7.73(d, J=8.8 Hz, 1H), 7.96(s, 1H), 8.99(br, 1H); 10.78(br, 1H).

EXAMPLE 6

Synthesis of Methyl 4-benzyl-1-(4-methoxy-benzenesulfonyl)-5-oxo-piperazine-2-carboxylate A title compound was prepared by the same method as in Example 4, except that the compound of Example 3 and benzylamine were used.

$^1$H NMR (CDCl$_3$, 400 MHz) δ 3.33(s, 3H), 3.52(dd, J=12.5, 1.9 Hz, 1H), 3.66(dd, J=12.6, 4.6 Hz, 1H), 3.87(s, 3H), 4.04(d, J=17.1 Hz, 1H), 4.18(d, J=14.6 Hz, 1H), 4.27(d, J=17.1 Hz, 1H), 4.78(d, J=4.6 Hz, 1H), 4.87(d, J=14.6 Hz, 1H), 6.97(d, J=9.0 Hz, 2.H), 7.13(m, 2H), 7.28(m, 3H), 7.71(dd, J=7.1, 1.9 Hz, 1H).

EXAMPLE 7

Synthesis of 4-Benzyl-1-(4-methoxy-benzenesulfonyl)-5-oxo-piperazine-2-hydroxamate A title compound was prepared by the same method as in Example 5, except the compound of Example 6 was used.

$^1$H NMR (DMSO-d$_6$, 400 MHz) δ 3.23(dd, J=13.2, 5.3 Hz, 1H), 3.33(dd, J=12.6, 3.9 Hz, 1H), 3.84(s, 3H), 4.08(m, 3H), 4.34(t, 1H), 4.58(d, J=15.1 Hz, 1H), 6.95(m, 2H), 7.09(d, J=9.0 Hz, 2H), 7.23(m, 3H), 7.74(d, J=8.8 Hz, 2H), 8.99(br, 1H), 10.85(s, 1H).

EXAMPLE 8

Synthesis of Methyl 1-(4-methoxy-benzenesulfonyl)-5-oxo-4-(2-piperidin-1-yl-ethyl)-piperazine-2-carboxylate A title compound was prepared by the same method as in Example 4, except that a yellow oily title compound (yield 83%) was prepared using the compound of Example 3 and 1-(2-aminoethyl)piperidine(1-(2-aminoethyl)piperidine).

$^1$H NMR (CDCl$_3$, 400 MHz) δ 1.41(m, 2H), 1.51(m, 4H), 2.36(m, 6H), 3.43(t, J=6.6 Hz, 2H), 3.54(s, 3H), 3.77(dd, J=12.4, 2.2 Hz, 1H), 3.83(dd, J=12.6 4.6 Hz, 1H), 3.87(s, 3H), 3.90(d, J=17.1 Hz, 1H), 4.17(d, J=16.8 Hz, 1H), 4.82(s, 1H), 6.98(d, J=8.8 Hz, 2H), 7.72(d, J=8.8 Hz, 2H).

EXAMPLE 9

Synthesis of 1-(4-Methoxy-benzenesulfonyl)-5-oxo-4-(2-piperidin-1-yl-ethyl)-piperazine-2-hydroxamate hydrochloride A title compound was prepared by the same method as in Example 5, except that it was prepared from the compound of Example 8 and then treated with HCl, and recrystallized with MeOH/ether to obtain a light yellow solid (yield 31%).

$^1$H NMR (CDCl$_3$, 400 MHz)δ 1.42(br s, 2H), 1.56(m, 4H), 2.42(br m, 6H), 3.48(t, J=6.6 Hz, 2H), 3.65-3.82(br m, 2H), 3.85(s, 3H), 4.00-4.14(m, 2H), 4.62(br s, 1H), 6.98(d, J=8.3 Hz, 2H), 7.72(d, J=8.6 Hz, 2H), 9.21 (br, 1H).

EXAMPLE 10

Synthesis of Methyl 1-(4-methoxy-benzenesulfonyl)-4-(2-morpholin-4-yl-ethyl)-5-oxo-piperazine-2-carboxylate A title compound was prepared by the same method as in Example 4, except that the compound of Example 3 and N-(2-aminoethyl)morpholine were used to prepare a yellow oil (yield 74%).

$^1$H NMR (CDCl$_3$, 400 MHz) δ 2.43(m, 6H), 3.45(m, 2H), 3.53(s, 3H), 3.64(m, 3H), 3.75(m, 1H), 3.82(m, 1H), 3.87(s, 3H), 3.90(d, J=17.1 Hz, 1H), 4.17 (d, J=16.8 Hz, 1H), 4.84(s, 1H), 6.99(d, J=9.0 Hz, 2H), 7.73(d, J=8.8 Hz, 2H).

EXAMPLE 11

Synthesis of 1-(4-Methoxy-benzenesulfonyl)-4-(2-morpholin-4-yl-ethyl)-5-oxo-piperazine-2-hydroxamate hydrochloride A title compound was prepared by the same method as in Example 5, except that it was prepared from the compound of Example 10 and treated with HCl, and recrystallized with MeOH/ether to obtain a white solid.

EXAMPLE 12

Synthesis of Methyl 1-(4-methoxy-benzenesulfonyl)-5-oxo-4-pyridin-2-yl-methyl-piperazine-2-carboxylate A title compound was prepared by the same method as in Example 4, except that it was prepared from the compound of Example 3 and 2-aminomethylpyridine, and recrystallized with ethylacetate/hexane to obtain a white solid (yield 85%).

$^1$H NMR (CDCl$_3$, 400 MHz) δ 3.41 (s, 3H), 3.75-3.90(m, 2H), 3.91 (s, 3H), 4.03(d, J=17.1 Hz, 1H), 4.26(d, J=17.1 Hz, 1H), 4.46(d, J=3.2 Hz, 1H), 4.82(m, 1H), 4.84(s, 1H), 6.97(d, J=9.0 Hz, 2H), 7.17(m, 2H), 7.62(m, 1H), 7.72(d, J=9.0 Hz, 2H), 8.49(s,1H).

EXAMPLE 13

Synthesis of 1-(4-Methoxy-benzenesulfonyl)-5-oxo-4-pyridin-2-yl-methyl-piperazine-2-hydroxamate hydrochloride A title compound was prepared by the same method as in Example 5, except that it was prepared from the compound of Example 12 and treated with HCl, and recrystallized with MeOH/ether to obtain a white solid (yield 48%).

EXAMPLE 14

Synthesis of Methyl 1-(4-methoxy-benzenesulfonyl)-5-oxo-4-(2-pyridin-2-yl-ethyl)-piperazine-2-carboxylate A title compound was prepared by the same method as in Example 4, except that the compound of Example 3 and 2-(2-aminoethyl)pyridine were used to prepare an oil (yield 74%).

$^1$H NMR (CDCl$_3$, 400 MHz) δ 2.94(m, 2H), 3.49(s, 3H), 3.69(t, 2H), 3.74(t, J=7.3 Hz, 2H), 3.87(s, 3H), 3.89(d, J=17.1 Hz, 1H), 4.14(d, J=16.8 Hz, 1H), 4.79(t, J=3.7, 2.9 Hz, 1H), 6.98(d, J=8.8 Hz, 2H), 7.14(t, 2H), 7.59(td, J=7.6, 1.7 Hz, 1H), 7.72(d, J=8.6 Hz, 2H), 8.49(d, J=4.9 Hz, 1H).

EXAMPLE 15

Synthesis of 1-(4-Methoxy-benzenesulfonyl)-5-oxo-4-(2-pyridin-2-yl-ethyl-piperazine-2-hydroxamate A title compound was prepared by the same method as in Example 5, except that it was prepared from the compound of Example 14, and recrystallized with ethyl acetate/hexane to obtain a brown title compound (yield 29%).

EXAMPLE 16

Synthesis of Methyl 4-cyclopropyl-1-(4-methoxy-benzenesulfonyl)-5-oxo-piperazine-2-carboxylate A title compound was prepared by the same method as in Example 4, except that it was prepared from the compound of Example. 3 and cyclopropylamine, and recrystallized with ethylacetate/hexane to obtain a white solid compound (yield 43%).

$^1$H NMR (CDCl$_3$, 400 MHz) δ 0.46(m, 1H), 0.58(m, 1H), 0.77(m, 1H), 0.85(m, 1H), 2.62 (m, 1H), 3.56(s, 3H), 3.67(m, 2H), 3.83-3.87(m, 1H), 3.88(s, 3H), 4.12-4.18(m, 1H), 4.82(m, 1H), 6.99(m, 2H), 7.72(m, 2H).

EXAMPLE 17

Synthesis of 4-Cyclopropyl-1-(4-methoxy-benzenesulfonyl)-5-oxo-piperazine-2-hydroxamate A title compound was prepared by the same method as in Example 5, except that it was prepared from the compound of Example 16, and recrystallized with ethylacetate/MeOH/hexane to obtain a white solid compound (yield 49%).

EXAMPLE 18

Synthesis of Methyl 4-butyl-1-(4-1-methoxy-benzenesulfonyl)-5-oxo-piperazine-2-carboxylate A title compound was prepared by the same method as in Example 4, except that the compound of Example 3 and n-butylamine were used to prepare an oily title compound (yield 80%).

$^1$H NMR (CDCl$_3$, 400 MHz) δ 0.88(t, J=7.3 Hz, 3H), 1.24(m, 2H), 1.40(m, 2H), 3.20(m, 1H), 3.45(m, 1H), 3.55(s, 3H), 3.64(dd, J=12.7, 2.2 Hz, 1H), 3.72(dd, J=12.7, 4.4 Hz, 1H), 3.87(s, 3H), 3.89(d, J=16.3 Hz, 1H), 4.16(d, J=16.8 Hz, 1H), 4.86(dd, J=4.4, 2.2 Hz, 1H), 6.99(d, J=9.7 Hz, 2H), 7.73(d, J=8.8 Hz, 2H).

EXAMPLE 19

Synthesis of 4-Butyl-1-(4-methoxy-benzenesulfonyl)-5-oxo-piperazine-2-hydroxamate A title compound was prepared by the same method as in Example 5, except that it was prepared from the compound of Example 18, and recrystallized with CH$_2$Cl$_2$ to obtain a white title compound (yield 51%).

$^1$H NMR (DMSO-d$_6$, 400 MHz) δ 0.76(m, 3H), 0.97-1.19(m, 2H), 2.91(m, 1H), 3.22(m,1H), 3.29-3.41 (m, 2H), 3.83(s, 3H), 3.86(d, J=16.6 Hz, 1H), 3.95(d, J=16.8 Hz, 1H), 4.32(t, J=4.5 Hz, 1H), 7.10(d, J=9.0 Hz, 2H), 7.74(d, J=8.8 Hz, 2H), 8.99(s, 1H), 10.86(s, 1H).

EXAMPLE 20

Synthesis of Methyl 4-allyl-1-(4-methoxy-benzenesulfonyl)-5-oxo-piperazine-2-carboxylate A title compound was prepared by the same method as in Example 4, except that the compound of Example 3 was used to prepare an oily compound (yield 84%).

$^1$H NMR (CDCl$_3$, 400 MHz) δ 3.55(s, 3H), 3.62(dd, J=12.7, 2.2 Hz, 1H), 3.69(dd, J=12.7, 4.6 Hz, 1H), 3.79(dd, J=15.1, 6.6 Hz, 1H), 3.88(s, 3H), 3.93(d, J=17.1 Hz, 1H), 4.12(dd, J=14.8, 5.9 Hz, 1H), 4.20(d, J=16.8 Hz, 1H), 4.86(dd, J=4.6, 2.2 Hz, 1H), 5.13(dd, J=17.1, 1.4 Hz, 1H), 5.19(dd, J=10.1, 1.1 Hz, 1H), 5.58(m, 1H), 6.99(d, J=9.1 Hz, 2H), 7.73(d, J=9.0 Hz, 2H).

EXAMPLE 21

Synthesis of 4-Allyl-1-(4-methoxy-benzenesulfonyl)-5-oxo-piperazine-2-hydroxamate A title compound was prepared by the same method as in Example 5, except that it was prepared from the compound of Example 20 and recrystallized with CHCl$_3$ to obtain a white solid (yield 66%).

EXAMPLE 22

Synthesis of Methyl 1-(4-methoxy-benzenesulfonyl)-5-oxo-4-prop-2-ynyl-piperazine-2-carboxylate A title compound was prepared by the same method as in Example 4, except that it was prepared from the compound of Example 3 and propargylamine, and recrystallized with CH$_3$Cl/hexane to obtain a white solid (yield 90%).

$^1$H NMR (CDCl$_3$, 400 MHz) δ 2.16(s, 1H), 3.49(s, 3H), 3.72(dd, J=12.5, 4.6 Hz, 1H), 3.69(dd, J=12.7, 2.2 Hz, 1H), 3.81 (s, 3H), 3.86(d, J=17.1 Hz, 1H), 4.06(dd, J=17.3, 2.4 Hz, 1H), 4.14(d, J=17.1 Hz, 1H), 4.19(dd, J=17.6, 2.4 Hz, 1H), 4.84(dd, J=4.5, 2.0 Hz, 1H), 6.92(d, J=9.0 Hz, 2H), 7.66(d, J=9.0 Hz, 2H).

EXAMPLE 23

Synthesis of 1-(4-Methoxy-benzenesulfonyl)-5-oxo-4-prop-2-ynyl-piperazine-2-hydroxamate A title compound was prepared by the same method as in Example 5, except that it was prepared from the compound of Example 22, and recrystallized with ethylacetate/hexane to obtain a white crystal (yield 35%).

EXAMPLE 24

Synthesis of Methyl 1-(4-methoxy-benzenesulfonyl)-4-methyl-5-oxo-piperazine-2-carboxylate A title compound was prepared by the same method as in Example 4, except that it was prepared from the compound of Example 3 and methylamine, and recrystallized with ethylacetate/hexane to obtain a white solid (yield 73%)

$^1$H NMR (CDCl$_3$, 400 MHz) δ 2.94(s, 3H), 3.57(s, 3H), 3.64(dd, J=12.4, 1.8 Hz, 1H), 3.77(dd, J=12.7, 4.8 Hz, 1H), 3.87(d, J=16.8 Hz, 1H), 3.88(s, 3H), 4.17(d, J=16.8 Hz, 1H), 4.87(dd, J=4.6, 1.6 Hz, 1H), 6.98(d, J=11.9 Hz, 2H), 7.73(d, J=9.0 Hz, 2H).

EXAMPLE 25

Synthesis of 1-(4-Methoxy-benzenesulfonyl)-4-methyl-5-oxo-piperazine-2-hydroxamate A title compound was prepared by the same method as in Example 5; except that it was prepared from the compound of Example 24, and recrystallized with ethylacetate/MeOH/hexane to obtain a white solid (yield 52%).

$^1$H NMR (DMSO-d$_6$, 400 MHz) δ 2.67(s, 3H), 3.39(m, 2H), 3.82(d, J=16.4 Hz, 1H), 3.84(s, 3H), 3.93(d, J=16.4 Hz, 1H), 4.42(t, J=4.0 Hz, 1H), 7.10(d, J=9.0 Hz, 2H), 7.74(d, J=9.0 Hz, 2H), 8.98(s, 1 H), 10.82(s,1H).

EXAMPLE 26

Synthesis of 4-Butyl-1-(4-methoxy-benzenesulfonyl)-5-oxo-piperazine-2-carboxylic acid The compound of Example 18 (0.6 g, 1.56 mmol) was dissolved in 8 mL of methanol, and 2 ml of 2N NaOH were added dropwise while maintaining the temperature at 0° C. After stirring at room temperature for 6 hours, 20 mL of distilled water were added, and it was extracted with ethyl ether. A 2N HCl solution was added to control the pH of the aqueous solution layer to 1-2, and then the reactant was extracted with ethylacetate. The supernatant was collected, and dried and concentrated under reduced pressure, and then recrystallized with ethylacetate/hexane to obtain a light yellow solid compound (0.51 g, yield 88%).

$^1$H NMR (CDCl$_3$, 400 MHz) δ 0.86(t, 3H), 1.20(m, 2H), 1.39(m, 2H), 3.27(m, 1H), 3.34(m, 1H), 3.68(d, J=3.2 Hz, 2H), 3.86(s, 3H), 3.93(d, J=17.3 Hz, 1H), 4.17(d, J=17.3 Hz, 1H), 4.84(t, J=3.2 Hz, 1H), 6.97(d, J=9.0 Hz, 2H), 7.74(d, J=8.8 Hz, 2H).

EXAMPLE 27

Synthesis of 1-Cyclopropyl-5-hydroxymethyl-4-(4-methoxy-benzenesulfonyl)-5-oxo-piperazin-2-one The compound of Example 16 (1.13 g, 3.06 mmol) was dissolved in 10 mL of methanol, and NaBH$_4$ (0.35 g, 10.8 mmol) was added dropwise while maintaining the temperature at 0° C. After stirring at room temperature for 16 hours, 20 mL of distilled water were added and the reactant was concentrated under reduced pressure. Ethyl acetate was added to the aqueous solution layer, the organic layer was dried and concentrated under reduced pressure, and then it was recrystallized with ethylacetate/hexane to obtain a white solid compound (0.56 g, yield 54%).

$^1$H NMR (CDCl$_3$, 400 MHz) δ 0.24(m, 1H), 0.31(m, 1H), 0.70(m, 2H), 2.50(m, 1H), 3.27(dd, J=13.4, 5.6 Hz, 1H), 3.38(dd, J=13.2, 5.6 Hz,1H), 3.66(dd, J=10.9, 6.8 Hz, 1H), 3.75(dd, J=11.2, 5.2 Hz, 1H), 3.80(d, J=17.3 Hz, 1H), 3.88(s, 3H), 4.08(dd, J=17.1 Hz, 1H), 6.99(d, J=8.8 Hz, 2H), 7.73(d, J=8.8 Hz, 2H).

EXAMPLE 28

Synthesis of 1-Cyclopropyl-5-mercaptomethyl-4-(4-methoxy-benzesulfonyl)-5-oxo-piperazin-2-one The compound of Example 27 (0.62 g, 1.82 mmol) was dissolved in 25 mL of THF, and PPh$_3$ (0.59 g, 2.2 mmol) and thiolacetic acid (0.16 mL, 2.2 mmol) were added dropwise while maintaining the temperature at 0° C., and then diethylazodicarboxylate (0.38 mL, 2.2 mmol) was added. After stirring at room temperature for 16 hours, 20 mL of distilled water were added and it was concentrated under reduced pressure. Ethylacetate was added to the aqueous solution layer, and the organic layer was dried and concentrated under reduced pressure. 15 mL of methanol was dissolved therein and 2 mL of 2N NaOH were added dropwise while maintaining the temperature at 0° C. After stirring at room temperature for 6 hours, 20 mL of distilled water were added and the reactant was extracted with ethyl acetate. The supernatant was collected, and dried and concentrated under reduced pressure, and then it was recrystallized with ethyl acetate/hexane to obtain a light yellow solid (0.10 g; yield 15%).

$^1$H NMR (CDCl$_3$, 400 MHz) δ 0.27(m, 1H), 0.36(m, 1H), 0.81 (m, 2H), 2.47(m, 1H), 3.31(br, 1H), 3.38(br, 1H), 3.73(m, 2H), 3.80(d, J=17.1 Hz, 1H), 3.88(s, 3H), 4.08(dd, J=16.8 Hz, 1H), 6.95(d, J=8.8 Hz, 2H), 7.75(d, J=8.8 Hz, 2H).

EXAMPLE 29

Synthesis of Methyl 2-(4'-bromo-biphenyl-4-sulfonylamino)-3-hydroxy-propionate D-serine methylester HCl of the Chemical Formula 5 (5.62 g, 36.1 mmol) was suspended in 130 mL of dichloromethane, and Et$_3$N (11 Ml, 76.5 mmol) and a catalytic amount of 4-dimethylaminopyridine were added while maintaining the temperature at 0° C., and 4-bromobiphenyl sulfonyl chloride (12.0 g, 36.2 mmol) were added dropwise. After stirring at room temperature for 20 hours, the reactant was washed with a 1N HCl aqueous solution (50 mL), a saturated NaHCO$_3$ aqueous solution (50 mL), and distilled water (100 mL), and it was dried and concentrated under reduced pressure to obtain a white solid title compound (14.0 g, yield 93%).

$^1$H NMR (CDCl$_3$, 400 MHz) δ 3.57(s, 3H), 3.86(dd, J=3.7, 1.7 Hz, 1H), 3.89(dd, J=3.6, 1.7 Hz, 1H), 4.05(m, 1H), 7.47(d, J=8.0 Hz, 2H), 7.60(d, J=8.3 Hz, 2H), 7.67(d, J=8.3 Hz, 2H), 7.91 (d, J=8.0 Hz, 2H).

EXAMPLE 30

Synthesis of Methyl 2-[(4'-bromo-biphenyl-4-sulfonylamino)-[ethoxycarbonylmethyl-amino]-3-hydroxy-propionate The compound of Example 29 (1.72 g, 4.15 mmol) and potassium carbonate anhydride (1.7 g, 12.4 mmol) were suspended in DMF (10 Ml), and then a catalytic amount of Et$_3$N and ethyl bromoacetate (0.92 mL, 8.3 mmol) were added dropwise. After stirring for 8 hours, 50 mL of distilled water and 100 mL of ethylacetate were introduced and stirred to separate layers. The supernatant was Washed with 50 Ml of a 1N HCl aqueous solution, 50 mL of a saturated NaHCO$_3$ aqueous solution, and 10 mL of distilled water, and it was dried and concentrated under reduced pressure. The mixture was separated with hexane and ethyl acetate (1:1) in a silica gel column, and recrystallized with hexane and ethyl acetate to obtain a white title compound (1.81 g, yield 87%).

$^1$H NMR (CDCl$_3$, 400 MHz) δ 1.31(t, J=6.8 Hz, 3H), 3.59(s, 3H), 3.63(m, 1H), 3.99(d, J=18.4 Hz, 1H), 4.04(m, 1H), 4.25(m, 2H), 4.47(d, J=19.2 Hz, 1H), 4.80(dd, J=9.2, 4.0 Hz, 1H), 7.47(d, J=8.8 Hz, 2H), 7.60(d, J=8.8 Hz, 2H), 7.67(d, J=8.0 Hz, 2H), 7.90(d, J=8.4 Hz, 2H).

EXAMPLE 31

Synthesis of Methyl 1-(4'-bromo-biphenyl-4-sulfonyl)-4-octyl-5-oxo-piperazine-2-carboxylate The compound of Example 29 (2.13 g, 4.25 mmol) was suspended in 40 mL of dichloromethane, and then Et$_3$N (0.83 mL, 5.9 mmol) and methane sulfonyl chloride (0.43 mL, 5.52 mmol) were added dropwise while maintaining the temperature at 0° C. After stirring at room temperature for 4 hours, the temperature was lowered to 0° C., and 20 mL of dichloromethane in which Et$_3$N (1.2 mL, 8.5 mmol) and octylamine (2.1 mL, 12.7 mmol) were dissolved were added. After stirring at room temperature for 16 hours, the reactant was washed with distilled water, 2N HCl, and a saturated NaHCO$_3$ aqueous solution, and then it was dried and concentrated under reduced pressure. The mixture was separated with ethyl acetate/hexane (4:1) in a silica gel column, and recrystallized with hexane and ethyl acetate to obtain a white title compound (1.35 g, yield 56%).

$^1$H NMR (CDCl$_3$, 400 MHz) δ 0.86(t, J=6.9 Hz, 3H), 1.23(m, 12H), 1.40(m, 2H), 3.21(m, 1H), 3.42(m, 1H), 3.53(s, 3H), 3.68(dd, J=12.6, 2.1 Hz, 1H), 3.76(dd, J=12.4, 4.4 Hz, 1H), 3.93(d, J=16.8 Hz, 1H), 4.23(d, J=16.8 Hz, 1H), 4.90(m, 1H), 7.47(d, J=8.1 Hz, 2H), 7.62(d, J=8.3 Hz, 2H), 7.70(d, J=8.3 Hz, 2H), 7.86(d, J=8.3 Hz, 2H).

EXAMPLE 32

Synthesis of 1-(4'-Bromo-biphenyl-4-sulfonyl)-4-octyl-5-oxo-piperazine-2-hydroxamate To the compound of Example 29 (0.51 g, 0.9 mmol), 6 mL of a 1.7 M H$_2$NOH solution (prepared from hydroxylamine and KOH according to Fieser and Fieser, Vol. 1, p 478 method) were added and stirred for 3 hours. After 5 hours, the reactant was acidified with a 2N HCl aqueous solution and made pH neutral with a saturated NaHCO$_3$ aqueous solution, and then it was extracted with ethyl acetate, and dried and concentrated under reduced pressure. It was recrystallized with THF/hexane to obtain a white solid title compound (0.12 g, yield 24%).

$^1$H NMR (DMSO-d$_6$, 400 MHz) δ 0.79(t, J=7.3 Hz, 3H), 0.93-1.17(m, 12H), 3.23-3.29(m, 2H), 3.38(m, 2H), 3.98(m, 2H), 4.38(t, J=4.6 Hz, 1H), 7.71(m, 4H), 7.89(m, 4H), 9.04(s, 1H), 10.91(s, 1H); $^{13}$H NMR (DMSO-d$_6$, 100 MHz) δ 14.35, 22.41, 26.42, 26.81, 28.98, 29.07, 31.62, 45.97, 47.22, 47.31, 53.19, 122.78, 127.83, 128.47, 129.53, 132.44, 136.90, 137.66, 143.81, 164.41, 165.04.

EXAMPLE 33

Synthesis of 1-(4'-Bromo-biphenyl-4-sulfonyl)-4-octyl-5-oxo-piperazine-2-carboxylic acid The compound of Example 29 (0.45 g, 0.79 mmol) was dissolved in 7 mL of THF, and 1.2 mL of 2N NaOH were added dropwise at 0° C. After stirring room temperature for 3 hours, the reactant was concentrated under reduced pressure, acidified with a 2 N HCl aqueous solution, and then extracted with ethyl acetate, and dried and concentrated under reduced pressure. It was recrystallized with hexane and ethyl acetate to obtain a white title compound (0.34 g, yield 77%).

$^1$H NMR (CDCl$_3$, 400 MHz) δ 0.86(t, J=6.9 Hz, 3H), 1.20(br s, 10H), 1.38(m, 2H), 3.16(m, 1H), 3.37(m, 1H), 3.65(dd, J=12.4, 2.0 Hz, 1H), 3.70(dd, J=12.7, 4.4 Hz, 1H), 3.95(d, J=17.1 Hz, 1H), 4.17(d, J=17.3 Hz, 1H), 4.34(br, 1H), 4.85(s, 1H), 7.46(d, J=8.6 Hz, 2H), 7.59(d, J=8.6 Hz, 2H), 7.67(d, J=8.6 Hz, 2H), 7.84(d, J=8.5 Hz, 2H); $^{13}$H NMR (CDCl3, 100 MHz) δ 14.06, 22.58, 26.62, 29.16, 31.73, 45.74, 47.51, 48.06, 48.50, 53.53, 123.15, 127.52, 127.56, 127.58, 128.12, 128.86, 132.25, 136.87, 137.88, 170.41.

EXAMPLE 34

Synthesis of Methyl 1-(4'-bromo-biphenyl-4-sulfonyl)-5-oxo-4-prop-2-ynyl-piperazine-2-carboxylate Title compound was prepared by the same method as in Example 31, except propargyl amine was used as the primary amine.

EXAMPLE 35

Synthesis of 1-(4'-Bromo-biphenyl-4-sulfonyl)-5-oxo-4-prop-2-ynyl-piperazine-2-carboxylic acid A title compound was prepared by the same method as in Example 33, except the compound of Example 34 was used.

EXAMPLE 36

Synthesis of Methyl 4-benzyl-1-(4'-bromo-biphenyl-4-sulfonyl)-5-oxo-piperazine-2-carboxylate A title compound was prepared by the same method as in Example 31, except benzylamine was used as the primary amine.

EXAMPLE 37

Synthesis of 4-Benzyl-1-(4'-bromo-biphenyl-4-sulfonyl)-5-oxo-piperazine-2-carboxylic acid A title compound was prepared by the same method as in Example 33, except the compound of Example 36 was used.

EXAMPLE 38

Synthesis of Methyl 1-(4'-bromo-biphenyl-4-sulfonyl)-4-dodecyl-5-oxo-piperazine-2-carboxylate A title compound was prepared by the same method as in Example 31, except dodecylamine was used as the primary amine.

EXAMPLE 39

Synthesis of 1-(4'-Bromo-biphenyl-4-sulfonyl)-4-dodecyl-5-oxo-piperazine-2-carboxylic acid A title compound was prepared by the same method as in Example 33, except the compound of Example 38 was used.

EXAMPLE 40

Synthesis of Methyl 1-(4'-bromo-biphenyl-4-sulfonyl)-4-(3-butoxy-propyl)-5-oxo-piperazine-2-carboxylate A title compound was prepared by the same method as in Example 31, except 3-butoxypropylamine was used as the primary amine.

EXAMPLE 41

Synthesis of 1-(4'-Bromo-biphenyl-4-sulfonyl)-4-(3-butoxy-propyl)-5-oxo-piperazine-2-carboxylic acid A title compound was prepared by the same method as in Example 33, except the compound of Example 40 was used.

EXAMPLE 42

Synthesis of Methyl 1-(4'-bromo-biphenyl-4-sulfonyl)-4-(3-dimethylamino-propyl)-5-oxo-piperazine-2-carboxylate A title compound was prepared by the same method as in Example 31, except 3-(dimethylamino)propylamine was used as the primary amine.

EXAMPLE 43

Synthesis of 1-(4'-Bromo-biphenyl-4-sulfonyl)-4-(3-dimethylamino-propyl)-5-oxo-piperazine-2-carboxylic acid A title compound was prepared by the same method as in Example 33, except the compound of Example 42 was used.

EXAMPLE 44

Synthesis of Methyl 1-(4'-bromo-biphenyl-4-sulfonyl)-4-hexyl-5-oxo-piperazine-2-carboxylate A title compound was prepared by the same method as in Example 31, except hexylamine was used as the primary amine. m.p. 127-129° C.

EXAMPLE 45

Synthesis of 1-(4'-Bromo-biphenyl-4-sulfonyl)-4-hexyl-5-oxo-piperazine-2-carboxylic acid A title compound was prepared by the same method as in Example 33, except the compound of Example 44 was used.

EXAMPLE 46

Synthesis of Methyl 1-(4'-bromo-biphenyl-4-sulfonyl)-4-decyl-5-oxo-piperazine-2-carboxylate A title compound was prepared by the same method as in Example 31, except decylamine was used as the primary amine. m.p. 117-118° C.

EXAMPLE 47

Synthesis of 1-(4'-Bromo-biphenyl-4-sulfonyl)-4-decyl-5-oxo-piperazine-2-carboxylic acid A title compound was prepared by the same method as in Example 33, except the compound of Example 46 was used.

EXAMPLE 48

Synthesis of Methyl 1-(4'-bromo-biphenyl-4-sulfonyl)-4-butyl-5-oxo-piperazine-2-carboxylate A title compound was prepared by the same method as in Example 31, except butylamine was used as the primary amine. m.p. 113-115° C.

EXAMPLE 49

Synthesis of 1-(4'-Bromo-biphenyl-4-sulfonyl)-4-butyl-5-oxo-piperazine-2-carboxylic acid A title compound was prepared by the same method as in Example 33, except the compound of Example 38 was used.

EXAMPLE 50

Synthesis of Methyl 1-(4'-bromo-biphenyl-4-sulfonyl)-4-(6-hydroxy-hexyl)-5-oxo-piperazine-2-carboxylate A title compound was prepared by the same method as in Example 31, except 6-amino-1-hexanol was used as the primary amine.

EXAMPLE 51

Synthesis of 1-(4'-Bromo-biphenyl-4-sulfonyl)-4-(6-hydroxy-hexyl)-5-oxo-piperazine-2-carboxylic acid A title compound was prepared by the same method as in Example 33, except the compound of Example 50 was used.

EXAMPLE 52

Synthesis of Methyl 1-(4'-bromo-biphenyl-4-sulfonyl)-4-octadec-9-enyl-5-oxo-piperazine-2-carboxylate A title compound was prepared by the same method as in Example 31, except oleylamine was used as the primary amine. m.p. 108° C.

EXAMPLE 53

Synthesis of 1-(4'-Bromo-biphenyl-4-sulfonyl)-4-octadec-9-enyl-5-oxo-piperazine-2-carboxylic acid A title compound was prepared by the same method as in Example 33, except the compound of Example 52 was used.

EXAMPLE 54

Synthesis of 1-(4'-Methoxy-biphenyl-4-sulfonyl)-4-octyl-5-oxo-piperazine-2-carboxylic acid A title compound was prepared by the same method as in Example 33, except 3-methoxybiphenylsulfonyl chloride was used instead of 4-bromobiphenylsulfonyl chloride.

$^1$H NMR (CDCl$_3$, 400 MHz) δ 0.87(t, J=6.8 Hz, 3H), 1.20(br s, 10H), 1.46(t, J=6.6 Hz, 2H), 3.21(m, 1H), 3.44(m, 1H), 3.68(d, J=3.2 Hz, 2H), 3.88(s, 3H), 4.13(d, J=17.6 Hz, 1H), 4.32(d, J=17.4 Hz, 1H), 4.91(t, J=3.1 Hz, 1H), 7.03(d, J=8.5 Hz, 1H), 7.35(d, J=7.3 Hz, 2H), 7.43(d, J=7.9 Hz, 2H), 7.73(dd, J=8.5, 2.2 Hz, 1H), 8.14(d, J=2.2 Hz, 1H); $^{13}$H NMR (CDCl$_3$, 100 MHz) δ 14.07, 22.62, 26.71, 29.17, 31.76, 46.19, 47.56, 48.59, 53.63, 56.24, 112.77, 126.77, 127.12, 127.65, 129.01, 129.45, 133.40, 133.83, 156.11, 165.11, 170.93.

EXAMPLE 55

Synthesis of Methyl 2-[ethoxycarbonylmethyl-(4-nitro-benzenesulfonyl)-amino]-3-hydroxy-propionate Methyl 3-hydroxy-2-(4-nitro-benzenesulfonylamino)-propionate (4.0 g, 13.1 mmol) and potassium carbonate anhydride (5.45 g, 39.4 mmol) were suspended in DMF (25 mL), and ethyl bromoacetate (2.91 mL, 26.3 mmol) was added dropwise at 0° C. After stirring for 4 hours, 50 mL of distilled water and 100 mL of acetate were introduced and stirred to separate layers. The supernatant was washed with 50 mL of a 5% Na$_2$S$_2$O$_3$ aqueous solution, 50 mL of a 1N HCl aqueous solution, 50 mL of a saturated NaHCO$_3$ aqueous solution, and 100 mL of distilled water, and it was dried and concentrated under reduced pressure. The mixture was separated with hexane and ethylacetate (2:1) in a silica gel column to obtain a yellow oil (4.43 g, 86.5).

$^1$H NMR (CDCl$_3$, 400 MHz) δ 1.30(t, J=7.1 Hz, 3H), 3.63(m, 1H), 3.64(s, 3H), 3.92(dd, J=10.7, 3.4 Hz, 1H), 3.98(d, J=19.0 Hz, 1H), 4.02(dd, J=10.9, 3.9 Hz, 1H), 4.24(m, 2H), 4.45(d, J=19.0 Hz, 1H), 4.80(dd, J=9.3, 4.2 Hz, 1H), 8.03(d, J=8.8 Hz, 2H), 8.35(d, J=8.8 Hz, 2H); $^{13}$C NMR (CDCl$_3$, 100 MHz) δ 14.0, 46.4, 52.7, 60.3, 62.5, 62.6, 124.2, 128.9, 144.7, 150.6, 168.7, 171.6.

EXAMPLE 56

Synthesis of Methyl 1-(4-nitro-benzenesulfonyl)-4-octyl-5-oxo-piperazine-2-carboxylate A title compound was prepared by the same method as in Example 31, except that octylamine as the primary amine and the compound of Example 55 were used to obtain a white solid title compound (yield 88%).

$^1$H NMR (CDCl$_3$, 400 MHz) δ 0.86(t, J=6.9 Hz, 3H), 1.24(m, 10H), 1.43(m, 2H), 3.22(m, 1H), 3.44(m, 1H), 3.57(s, 3H), 3.72(d, J=12.7 Hz, 1H), 3.80(dd, J=12.7, 4.2 Hz, 1H), 3.86(d, J=16.6 Hz, 1H), 4.26(d, J=16.6 Hz, 1H), 4.91 (m, 1 H), 7.98(d, J=8.8 Hz, 2H), 8.36(d, J=8.8 Hz, 2H); m.p. 85-86° C.

EXAMPLE 57

Synthesis of Methyl 4-octyl-5-oxo-1-(4-pyrrol-1-yl-benzenesulfonyl)-piperazine-2-carboxylate The compound of Example 56 (0.69 g, 1.5 mmol) was put in 10 mL of a MeOH solution to which $SnCl_2 \cdot 2H_2O$ (1.37 g, 6.4 mmol) was added, and stirred for 1.5 hours while maintaining the temperature at 50° C. A saturated $NaHCO_3$ aqueous solution was introduced and stirred for 2 hours, and then it was extracted with ethyl acetate. After distillation under reduced pressure, 2,5-dimethoxytetrahydrofuran (0.20 mLo, 1.5 mmol) and 1 mL of acetic acid were introduced and refluxed for 2 hours. 50 mL of ethyl acetate was introduced and the reactant was washed with 50 mL of a saturated $NaHCO_3$ aqueous solution and 50 mL of a 1 N HCl aqueous solution, and dried and then concentrated under reduced pressure. The mixture was separated with hexane and ethyl acetate (3:1) in a silica gel column to obtain a yellow oily title compound (0.19 g, 26%).

$^1$H NMR ($CDCl_3$, 400 MHz) δ 0.86(t, J=6.8 Hz, 3H), 1.25(m, 10H), 1.39(m, 2H), 3.20(m, 1H), 3.43(m, 1H), 3.55(s, 3H), 3.74(m, 2H), 3.91(d, J=16.6 Hz, 1H), 4.22(d, J=16.8 Hz, 1H), 4.89(m, 1H), 6.41(t, J=2.4 Hz, 2H), 7.16(t, J=2.4 Hz, 2H), 7.52(d, J=8.8 Hz, 2H), 8.85(d, J=8.8 Hz, 2H).

EXAMPLE 58

Synthesis of 4-Octyl-5-oxo-1-(4-pyrrol-1-yl-benzenesulfonyl)-piperazine-2-carboxylic acid The compound of Example 57 (0.19 g, 0.4 mmol) was dissolved in 5 mL of THF, and 1 mL of 2N NaOH was added dropwise at 0° C. After reaction at room temperature for 3 hours, the reactant was concentrated under reduced pressure and acidified with a 2N HCl aqueous solution, extracted with ethyl acetate, and concentrated under reduced pressure. It was then recrystallized with hexane and ethyl acetate to obtain an ivory colored compound (0.07 g, yield 28%).

$^1$H NMR ($CDCl_3$, 400 MHz) δ 0.79(br, 3H), 1.07-1.15(m, 14H), 3.42(m, 1H), 3.74(m, 3H), 3.90(br, 1H), 4.23(br, 1H), 4.64(br, 1H), 6.34(s, 2H), 7.07(s, 2H), 7.40(br, 2H), 7.86(br, 2H).

EXAMPLE 59

Synthesis of Methyl 1-[4-(4-chloro-benzoylamino)-benzenesulfonyl]-4-octyl-5-oxo-piperazine-2-carboxylate The compound of Example 56 (0.55 g, 1.2 mmol) was put into 10 mL of a MeOH solution to which $SnCl_2 \cdot 2H_2O$ (1.1 g, 4.8 mmol) was added, and stirred for 1 hour while maintaining the temperature at 50° C. A saturated $NaHCO_3$ aqueous solution was introduced and the mixture was stirred for 1 hour, and then it was extracted with ethyl acetate. After distillation under reduced pressure and vacuum drying, the mixture was dissolved in 20 mL of dichloromethane and $Et_3N$ (0.41 mL, 2.9 mmol), and 4-chlorobenzoyl chloride (0.31 mL, 2.4 mmol) was added while maintaining the temperature at 0° C. After reaction for 6 hours, the reactant was washed with a saturated NaHCO3 aqueous solution and a 1N HCl aqueous solution, and dried and concentrated under reduced pressure. It was then recrystallized with hexane and ethyl acetate to obtain a white solid (0.62 g, 91%).

$^1$H NMR ($CDCl_3$, 400 MHz) δ 0.86(t, J=6.8 Hz, 3H), 1.27(m, 10H), 1.41(m, 2H), 3.20(m, 1H), 3.42(m, 1H), 3.56(s, 3H), 3.65(dd, J=12.7, 2.0 Hz, 1H), 3.75(dd, J=12.4, 4.4 Hz, 1H), 3.90(d, J=16.6 Hz, 1H), 4.17(d, J=16.6 Hz, 1H), 4.87(m, 1H), 7.48(d, J=8.5 Hz, 2H), 7.77(d, J=9.0 Hz, 2H), 7.84(d, J=8.8 Hz, 2H), 7.86(d, J=8.5 Hz, 2H), 8.33(s,1 H); m.p. 171-173° C.

EXAMPLE 60

Synthesis of 1-[4-(4-chloro-benzoylamino)-benzenesulfonyl]-4-octyl-5-oxo-piperazine-2-carboxylic acid The compound of Example 59 (0.56 g, 0.99 mmol) was dissolved in 8 mL of THF, and 2 mL of 2N NaOH were added dropwise while maintaining the temperature at 0° C. After stirring at room temperature for 2 hours, 20 mL of distilled water were added and a 2N HCl solution was further added to control the pH to 1-2, and then the reactant was extracted with ethyl acetate. The supernatant was collected, and dried and concentrated under reduced pressure, and then recrystallized with ethyl acetate/hexane to obtain a light yellow solid compound (0.15 g, yield 27%).

$^1$H NMR ($CDCl_3$, 400 MHz) δ 0.86(t, J=6.8 Hz, 3H), 1.23(m, 10H), 1.43(m, 2H), 3.32(m, 2H), 3.65(d, J=12.2 Hz, 1H), 3.78(m, 2H), 4.05(d, J=16.8 Hz, 1H), 4.84(s, 1H), 7.48(d, J=8.3 Hz, 2H), 7.53(d, J=8.3 Hz, 2H), 7.64(d, J=8.5 Hz, 2H), 7.93(d, J=8.3 Hz, 2H), 9.22(s, 1H); m.p. 151-154° C.

EXPERIMENT EXAMPLE

Experiment 1: Measurement of MMP Inhibiting Activities

Inhibitory activities of all the enzymes were measured similarly to the MMP-2 activity measuring method shown below. Prior to measuring, proMMP-2 was treated with 1 mM p-aminophenyl mercuricacetate at 37° C. for 45 minutes to activate it. The ProMMP-9 was activated to an enzyme with MMP-3, and stored at −80° C. until used.

MMP activities were measured by fluorescence assay by changing a microtiter plate formate according to the reported method (Knight, C. G., Willenbrock, F., Murphy, G. A., FEBS Lett. 1992, 296, 263-266). On a dynatech MicroFLUOR plate, a buffer solution comprising 50 Mm Tris-HCl pH 7.5, 10 mM $CaCl_2$, 0.15 M NaCl, 0.05% Brij, and 1-8 µM of a substrate (Mca-Pro-Leu-Gly-Leu-Dpa-Ala-Arg-$NH_2$), and various concentrations of inhibitors were introduced, and it was reacted with activated enzymes at 37° C. for 20-30 minutes. Reaction was terminated by putting the reactant in 50 mM EDTA, and then fluorescence was measured with a spectrofluorometer attached to a microplate reader (λex 328 nm, λ em 393 nm). The inhibiting activity degree was indicated by an $IC_{50}$ value, which is a concentration inhibiting activity by 50% compared to the control. Results were as shown in Table 1.

TABLE 1

| | Enzyme inhibiting constant $IC_{50}$ (µM) | | | | |
| --- | --- | --- | --- | --- | --- |
| | MMP-1 | MMP-2 | MMP-9 | MMP-13 | MMP-14 |
| Example 5 | | 0.004 | 0.0124 | | 0.028 |
| Example 7 | 0.052 | 0.007 | 0.025 | 0.018 | 0.036 |

TABLE 1-continued

| | Enzyme inhibiting constant | | | | |
| --- | --- | --- | --- | --- | --- |
| | | $IC_{50}$ (μM) | | | |
| | MMP-1 | MMP-2 | MMP-9 | MMP-13 | MMP-14 |
| Example 15 | >10 | >10 | | >10 | |
| Example 19 | 0.047 | 0.015 | | 0.014 | |
| Example 25 | 0.082 | 0.003 | | 0.016 | |
| Example 32 | 0.016 | 0.002 | 0.0013 | 0.007 | |
| Example 33 | 2.430 | 0.080 | | 2.100 | |
| Example 39 | 8.270 | 0.567 | | 2.350 | |
| Example 45 | 0.095 | 0.011 | | 0.082 | |
| Example 47 | 5.400 | 0.140 | | 2.460 | |
| Example 49 | 0.114 | 0.009 | | 1.130 | |
| Example 51 | 0.029 | 0.005 | | 0.019 | |
| Example 53 | >10 | 0.220 | | >10 | |
| Example 60 | 0.018 | 0.003 | 0.0032 | 0.024 | |

As shown in Table 1, the compound of the present invention is superior as a proteinase inhibitor.

Experiment 2: Measurement of Tube Formation Activity

In a culture flask previously coated with gelatin, HUVEC (human umbilical vein endothelial cell) cells cultured with a M199 medium (containing 20% FBS, 3 ng/ml bFGF, 100 μg/ml heparin) were treated with trypsin/EDTA, and then number of cells are counted so that number of cells may be $2\times10^4$ cells/well in a 96-well plate previously coated with matrigel. Samples were then added and cultured in a $CO_2$ culture medium at 37° C. for 16-24 hours. After cultivation, whether or not endothelial cells were differentiated into capillary tubes was observed with a microscope, and activities were judged on the following basis. Results were as shown in Table 2.

TABLE 2

| | Tube Formation (concentration, μM) | | | |
| --- | --- | --- | --- | --- |
| | 100 | 50 | 5 | 0.5 |
| Control | − | − | − | − |
| Example 5 | ++ | + | ± | |
| Example 7 | | + | ± | |
| Example 9 | | ± | − | |
| Example 11 | | + | ± | |
| Example 13 | + | + | ± | |
| Example 15 | ++ | + | + | |
| Example 17 | ++ | + | + | |
| Example 19 | ++ | + | + | |
| Example 21 | | + | ± | |
| Example 23 | +++ | ++ | + | |
| Example 25 | + | − | − | |
| Example 26 | ++ | + | ± | |
| Example 27 | | ++ | ++ | |
| Example 32 | +++ | +++ | ++ | |
| Example 33 | +++ | ++ | + | |
| Example 35 | | +++ | ++ | ++ |
| Example 37 | | +++ | ++ | ++ |
| Example 39 | | + | − | − |
| Example 41 | | +++ | ++ | ++ |
| Example 43 | | ++ | ++ | + |
| Example 45 | | ++ | ++ | ++ |
| Example 47 | | +++ | ++ | ++ |
| Example 49 | | ++ | ++ | ± |

TABLE 2-continued

| | Tube Formation (concentration, μM) | | | |
| --- | --- | --- | --- | --- |
| | 100 | 50 | 5 | 0.5 |
| Example 58 | | ++ | ++ | ± |
| Example 60 | | ++ | ++ | + |

−: control
±: tube almost resembles control
+: inhibition
++: significant inhibition
+++: complete inhibition As shown in the above Table 2, the compounds of Examples 5 to 60 according to the present invention have superior angiogenesis inhibiting activities compared to the control. Therefore, the compound of the Chemical Formula 1 of the present invention can inhibit matrix metalloproteinase activity to efficiently control angiogenesis.

As explained, the compound of the Chemical Formula 1 of the present invention acts as a superior matrix metalloproteinase inhibitor and can be useful for a treating agent of various diseases related to angiogenesis such as cancer, periodontal disease, arthritis, etc., and it is particularly very effective for an anticancer drug capable of treating and preventing cancer.

What is claimed is:

1. A compound represented by the following Chemical Formula 1, optical isomers, pharmaceutically acceptable salts, or solvates thereof:

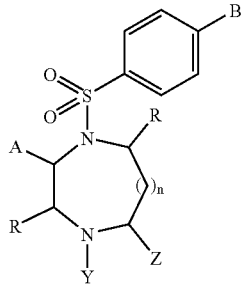

[Chemical Formula 1]

wherein,
n is 0, 2, or 3;
A is $CO_2H$, CONHOH, $CH_2SH$, or $CH_2OH$;
B is hydrogen; a C1-8 alkyl group; a nitro group; an aryl group; a heteroaryl group; a pyrrole group; a halogen atom; a C1-8 O-alkyl group; an O-aryl group; an N-alkyl group; an S-alkyl group;

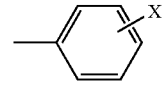

wherein X is hydrogen, a C1-8 alkyl group, a C9-20 alkyl group, a C9-20 alkenyl group, an aryl group, a heteroaryl group, a halogen atom, an O-alkyl group, an O-aryl group an O-heteroaryl group, an N-aryl group, an N-heteroaryl group, an S-aryl group, an S-heteroaryl group, a C1-20 alkyl-amine derivative, a C1-20 alkyl-carboxylic acid derivative, an amine group, or a nitro group); an amide compound of CONHR or NHCOR; a carbamate compound of NHCOOR;

or a urea compound of NHCONHR, wherein R is hydrogen, a C1-8 alkyl group, an aryl group, a heteroaryl group, a tetragonal to octagonal cyclic compound, a C1-8 alkyl group substituted by a tetragonal to octagonal cyclic compound, a tetragonal to octagonal heterocyclic compound, or a C1-8 alkyl group substituted by a tetragonal to octagonal heterocyclic compound;

R is hydrogen, a C1-8 alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 alkyl group substituted by a tetragonal to octagonal heterocyclic compound;

Z is oxygen, or sulfur, provided that in the case Z is oxygen or sulfur it takes a double bond;

Y is hydrogen; a C1-18 alkyl group; an aryl group; a heteroaryl; C1-8 alkyl group substituted by a tetragonal to octagonal cyclic compound; a C1-8 alkyl group substituted by a tetragonal to octagonal heterocyclic compound; an amide compound of CONHR or NHCOR; a carbamate compound of NHCOOR; a urea compound of NHCONHR; a C1-8 alkenyl group or alkynyl group; or a C9-20 alkenyl group or alkynyl group, wherein R is hydrogen, a C1-8 lower alkyl group, an aryl group, a heteroaryl, a tetragonal to octagonal cyclic compound, a C1-8 alkyl group substituted by a tetragonal to octagonal cyclic compound, a tetragonal to octagonal heterocyclic compound, or a C1-9 alkyl group substituted by a tetragonal to octagonal heterocyclic compound.

2. The compound according to claim 1, wherein A is CONHOH.

3. The compound according to claim 1, wherein A is $CO_2H$.

4. The compound according to claim 1, wherein A is $CH_2OH$.

5. The compound according to claim 1, wherein A is $CH_2SH$.

6. A process for preparing a compound of claim 2, comprising the step of reacting a compound of the following Chemical Formula 2 with $NH_2OH$ and KOH, or $NH_2OH$ in the presence of $AlCl_3$:

[Chemical Formula 2]

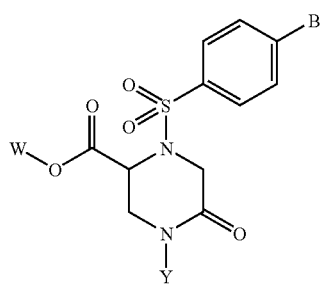

wherein,
B is hydrogen; a C1-8 lower alkyl group; a nitro group; an aryl group; a heteroaryl group; a pyrrole group; a halogen atom; a C1-8 O-lower alkyl group; an O-aryl group; an N-lower alkyl group; an S-lower alkyl group;

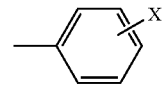

(X is hydrogen, a C1-8 lower alkyl group, a C9-20 higher alkyl group, a C9-20 higher alkyl group comprising a double bond, an aryl group, a heteroaryl group, a halogen atom, an O-lower alkyl group, an O-aryl group, an O-heteroaryl group, an N-aryl group, an N-heteroaryl group, an S-aryl group, an S-heteroaryl group, a C1-20 alkyl-amine derivative, a C1-20 alkyl-carboxylic acid derivative, an amine group, or a nitro group.); an amide compound of CONHR or NHCOR; a carbamate compound of NHCOOR; or a urea compound of NHCONHR (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound;

W is hydrogen, or a methyl, ethyl, t-butyl, or C1-8 lower alkyl group comprising a benzyl group;

Y is hydrogen; a C1-18 alkyl group; an aryl group; a heteroaryl; a C1-8 lower alkyl group substituted by a tetragonal to octagonal cyclic compound; a C1-8 lower alkyl group substituted by a tetragonal to octagonal heterocyclic compound; an amide compound of CONHR or NHCOR; a carbamate compound of NHCOOR; a urea compound of NHCONHR; a C1-9 lower alkyl group having a double bond or a triple bond; or a C9-20 higher alkyl group having a double bond or a triple bond (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound).

7. A process for preparing a compound of claim 3, comprising the step of hydrogenating a compound of the following Chemical Formula 2 in the presence of an inorganic base, an acid-base, or a Pd/C catalyst:

[Chemical Formula 2]

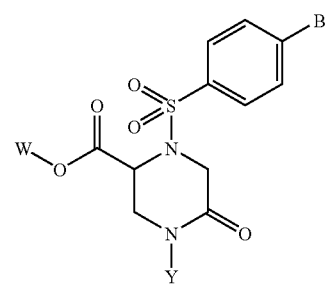

wherein,
B is hydrogen; a C1-8 lower alkyl group; a nitro group; an aryl group; a heteroaryl group; a pyrrole group; a halogen atom; a C1-8 O-lower alkyl group; an O-aryl group; an N-lower alkyl group; an S-lower alkyl group;

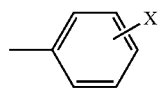

(X is hydrogen, a C1-8 lower alkyl group, a C9-20 higher alkyl group, a C9-20 higher alkyl group comprising a double bond, an aryl group, a heteroaryl group, a halogen atom, an O-lower alkyl group, an O-aryl group, an O-heteroaryl group, an N-aryl group, an N-heteroaryl group, an S-aryl group, an S-heteroaryl group, a C1-20 alkyl-amine derivative, a C1-20 alkyl-carboxylic acid derivative, an a mine group, or a nitro group.); an amide compound of CONHR or NHCOR; a carbamate compound of NHCOOR; or a urea compound of NHCONHR (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound;

W is hydrogen, or a methyl, ethyl, t-butyl, or C1-8 lower alkyl group comprising a benzyl group;

Y is hydrogen; a C1-18 alkyl group; an aryl group; a heteroaryl; a C1-8 lower alkyl group substituted by a tetragonal to octagonal cyclic compound; a C1-8 lower alkyl group substituted by a tetragonal to octagonal heterocyclic compound; an amide compound of CONHR or NHCOR; a carbamate compound of NHCOOR; a urea compound of NHCONHR; a C1-9 lower alkyl group having a double bond or a triple bond; or a C9-20 higher alkyl group having a double bond or a triple bond (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound).

8. A process for preparing a compound of claim 3, comprising the step of converting the ester group of a compound of the following Chemical Formula 2 into alcohol with a reductant comprising NaBH$_4$ in the presence of a solvent:

[Chemical Formula 2]

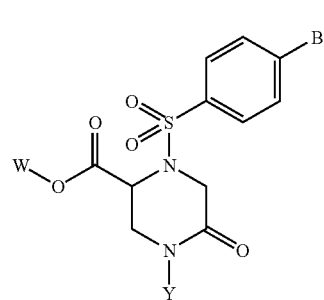

wherein,

B is hydrogen; a C1-8 lower alkyl group; a nitro group; an aryl group; a heteroaryl group; a pyrrole group; a halogen atom; a C1-8 O-lower alkyl group; an O-aryl group; an N-lower alkyl group; an S-lower alkyl group;

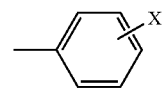

(X is hydrogen, a C1-8 lower alkyl group, a C9-20 higher alkyl group, a C9-20 higher alkyl group comprising a double bond, an aryl group, a heteroaryl group, a halogen atom, an O-lower alkyl group, an O-aryl group, an O-heteroaryl group, an N-aryl group, an N-heteroaryl group, an S-aryl group, an S-heteroaryl group, a C1-20 alkyl-amine derivative, a C1-20 alkyl-carboxylic acid derivative, an amine group, or a nitro group.); an amide compound of CONHR or NHCOR; a carbamate compound of NHCOOR; or a urea compound of NHCONHR (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound;

W is hydrogen, or a methyl, ethyl, t-butyl, or C1-8 lower alkyl group comprising a benzyl group;

Y is hydrogen; a C1-18 alkyl group; an aryl group; a heteroaryl; a C1-8 lower alkyl group substituted by a tetragonal to octagonal cyclic compound; a C1-8 lower alkyl group substituted by a tetragonal to octagonal heterocyclic compound; an amide compound of CONHR or NHCOR; a carbamate compound of NHCOOR; a urea compound of NHCONHR; a C1-9 lower alkyl group having a double bond or a triple bond; or a C9-20 higher alkyl group having a double bond or a triple bond (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound).

9. A compound represented by the following Chemical Formula 2, optical isomers, pharmaceutically acceptable salts, or solvates thereof:

[Chemical Formula 2]

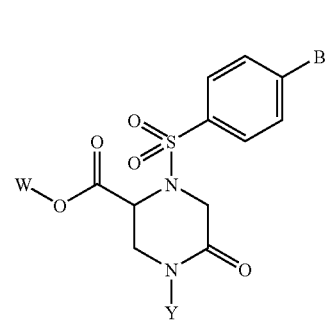

wherein,

B is hydrogen; a C1-8 lower alkyl group; a nitro group; an aryl group; a heteroaryl group; a pyrrole group; a halogen atom; a C1-8 O-lower alkyl group; an O-aryl group; an N-lower alkyl group; an S-lower alkyl group;

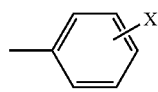

(X is hydrogen, a C1-8 lower alkyl group, a C9-20 higher alkyl group, a C9-20 higher alkyl group comprising a double bond, an aryl group, a heteroaryl group, a halogen atom, an O-lower alkyl group, an O-aryl group, an O-heteroaryl group, an N-aryl group, an N-heteroaryl group, an S-aryl group, an S-heteroaryl group, a C1-20 alkyl-amine derivative, a C1-20 alkyl-carboxylic acid derivative, an amine group, or a nitro group.); an amide compound of CONHR or NHCOR; a carbamate compound of NHCOOR; or a urea compound of NHCONHR (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound;

W is hydrogen, or a methyl, ethyl, t-butyl, or C1-8 lower alkyl group comprising a benzyl group;

Y is hydrogen; a C1-18 alkyl group; an aryl group; a heteroaryl; a C1-8 lower alkyl group substituted by a tetragonal to octagonal cyclic compound; a C1-8 lower alkyl group substituted by a tetragonal to octagonal heterocyclic compound; an amide compound of CONHR or NHCOR; a carbamate compound of NHCOOR; a urea compound of NHCONHR; a C1-9 lower alkyl group having a double bond or a triple bond; or a C9-20 higher alkyl group having a double bond or a triple bond (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound).

10. A process for preparing a compound of the following Chemical Formula 2, comprising the step of reacting a compound of the following Chemical Formula 3 with methanesulfonyl chloride, toluenesulfonyl chloride, or triflic anhydride in the presence of a base, and reacting it with a primary amine:

[Chemical Formula 2]

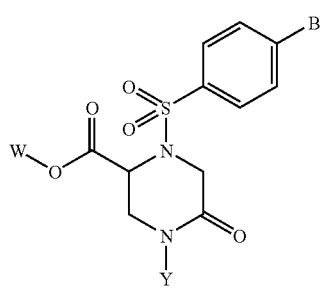

[Chemical Formula 3]

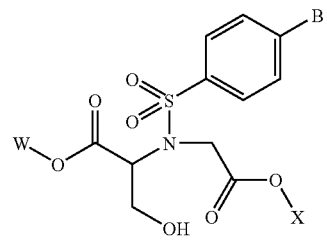

wherein,

B is hydrogen; a C1-8 lower alkyl group; a nitro group; an aryl group; a heteroaryl group; a pyrrole group; a halogen atom; a C1-8 O-lower alkyl group; an O-aryl group; an N-lower alkyl group; an S-lower alkyl group;

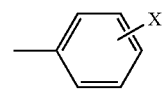

(X is hydrogen, a C1-8 lower alkyl group, a C9-20 higher alkyl group, a C9-20 higher alkyl group-comprising a double bond or a tr aryl group, a heteroaryl group, a halogen atom, an O-lower alkyl group, an O-aryl group, an O-heteroaryl group, an N-aryl group, an N-heteroaryl group, an S-aryl group, an S-heteroaryl group, a C1-20 alkyl-amine derivative, a C1-20 alkyl-carboxylic acid derivative, an amine group, or a nitro group.); an amide compound of CONHR or NHCOR; a carbamate compound of NHCOOR; or a urea compound of NHCONHR (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound;

W and X are independently or simultaneously hydrogen, or a methyl, ethyl, t-butyl, or C1-8 lower alkyl group comprising a benzyl group;

Y is hydrogen; a C1-18 alkyl group; an aryl group; a heteroaryl; a C1-8 lower alkyl group substituted by a tetragonal to octagonal cyclic compound; a C1-8 lower alkyl group substituted by a tetragonal to octagonal heterocyclic compound; an amide compound of CONHR or NHCOR; a carbamate compound of NHCOOR; a urea compound of NHCONHR; a C1-9 lower alkyl group having a double bond or a triple bond; or a C9-20 higher alkyl group having a double bond or a triple bond (R is hydrogen, a C1-8 lower alkyl group, an aryl group, a heteroaryl, a tetragonal to octagonal cyclic compound, a C1-8 lower alkyl group substituted by a tetragonal to octagonal cyclic compound, a tetragonal to octagonal heterocyclic compound, or a C1-8 lower alkyl group substituted by a tetragonal to octagonal heterocyclic compound).

11. A pharmaceutical composition comprising
a compound of the Chemical Formula 1 of claim 1, an optical isomer, a pharmaceutically acceptable salt, or a solvate thereof, as an active ingredient, and
a pharmaceutically acceptable carrier.

* * * * *